(12) United States Patent
Parks et al.

(10) Patent No.: US 7,932,503 B2
(45) Date of Patent: Apr. 26, 2011

(54) METHOD FOR PRE-IDENTIFICATION OF SPECTRAL OVERLAPS WITHIN FLUORESCENT DYE AND DETECTOR COMBINATIONS USED IN FLOW CYTOMETRY

(75) Inventors: David R. Parks, San Francisco, CA (US); Wayne Moore, San Francisco, CA (US); Stephen Meehan, Vancouver (CA)

(73) Assignees: David R. Parks, San Francisco, CA (US); Wayne Moore, San Francisco, CA (US); Stephen Meehan, Vancouver (CA)

( * ) Notice: Subject to any disclaimer, the term of this patent is extended or adjusted under 35 U.S.C. 154(b) by 43 days.

(21) Appl. No.: 12/467,662

(22) Filed: May 18, 2009

(65) Prior Publication Data

US 2010/0012853 A1    Jan. 21, 2010

Related U.S. Application Data

(60) Provisional application No. 61/053,974, filed on May 16, 2008.

(51) Int. Cl.
*G01N 21/64* (2006.01)

(52) U.S. Cl. .................................................. 250/459.1
(58) Field of Classification Search ............... 250/459.1
See application file for complete search history.

(56) References Cited

U.S. PATENT DOCUMENTS 7,593,158 B2 * 9/2009 Wilhelm et al. .............. 359/385

OTHER PUBLICATIONS

Velapoldi et al., "Corrected emission spectra and quantum yields for a series of fluorescent compounds in the visible spectral region," 2004, Journal of Fluorescence, vol. 14, No. 4, pp. 465-472.*

* cited by examiner

*Primary Examiner* — David P Porta
*Assistant Examiner* — Kiho Kim

(57) ABSTRACT

This invention relates to the field of flow cytometry. It provides methods for identifying important dye-detector spectral overlaps for use in designing flow cytometry experiments. It further provides methods for quantifying the impact of spectral overlaps on dye selection and detector selection, the methods including the steps of: a) obtaining spectra of a dye; b) obtaining a laser configuration and an optical filter configuration of a detector; c) obtaining a spectrum yield value; and d) ranking the spectrum yield value.

38 Claims, 12 Drawing Sheets

FIG. 8

Spectral overlap on "BD Flasher II™ : 3 laser; 2-5-4 configuration" by "Compensation test"

| | 407 - 545/90 (Cascade Yellow) | 488 - 525/50 (Fluorescein) | 488 - 575/25 (PhycoErythrin) | 488 - 665/30 (PE-Cy5) | 488 - 695/40 (PE-Cy5.5) | 488 - 785/45 (PE-Cy7) | 594 - 660/40 (AlloPhycoCyanin) | 594 - 710/40 (APC-Cy5.5) | 594 - 800/50 (APC-Cy7) |
|---|---|---|---|---|---|---|---|---|---|
| Monochlorobimane | 48 | 0 | 0 | 0 | 0 | 0 | 0 | 0 | 0 |
| Fluorescein (FITC) | 4 | 63 | 8 | 0 | 0 | 0 | 0 | 0 | 0 |
| R-PE | 2 | 0 | 27 | 1 | 2 | 0 | 0 | 0 | 0 |
| R-PE-Cy5 | 0 | 0 | 0 | 30 | 17 | 1 | 0 | 0 | 0 |
| R-PE-Cy5.5 | 0 | 0 | 0 | 4 | 27 | 5 | 0 | 0 | 0 |
| R-PE-Cy7 | 0 | 0 | 0 | 2 | 1 | 33 | 0 | 0 | 0 |
| APC | 0 | 0 | 0 | 0 | 0 | 0 | 33 | 9 | 0 |
| APC-Cy5.5 | 0 | 0 | 0 | 0 | 0 | 0 | 4 | 37 | 4 |
| APC-Cy7 | 0 | 0 | 0 | 0 | 0 | 0 | 2 | 1 | 28 |

FIG. 11

METHOD FOR PRE-IDENTIFICATION OF SPECTRAL OVERLAPS WITHIN FLUORESCENT DYE AND DETECTOR COMBINATIONS USED IN FLOW CYTOMETRY

CROSS REFERENCE

This application claims priority to U.S. Provisional Patent Application Ser. No. 61/053,974, filed May 16, 2008, incorporated by reference herein in its entirety.

FIELD OF INVENTION

This invention relates to the field of flow cytometry. More specifically, it relates to a method of identifying important dye-detector spectral overlaps for use in designing flow cytometry experiments.

BACKGROUND

Fluorescence

Fluorescence is a cyclical process where a luminescence is generated by certain molecules in which the molecular absorption of a photon triggers the emission of another photon with a longer wavelength.

In the fluorescence process, certain molecules are capable of being excited, via absorption of light energy, to a higher energy state, also called an excited state. The energy of this short-lived excited state decays (or decreases) resulting in the emission of light energy. The emission of light via this process is to "fluoresce."

A fluorophore is a molecule that is capable of fluorescing. In its ground state, the fluorophore molecule is in a relatively low-energy, stable configuration, and it does not fluoresce. When light from an external source hits a fluorophore molecule, the molecule can absorb the light energy. If the energy absorbed is sufficient, the molecule reaches an excited state (high energy); this process is known as excitation. There are multiple excited states or energy levels that the fluorophore can attain, depending on the wavelength and energy of the external light source. Since the fluorophore is unstable at high-energy configurations, it eventually adopts the lowest-energy excited state, which is semi-stable. The excited lifetime (the length of time that the fluorophore is an excited state) is very short; the fluorophore rearranges from the semi-stable excited state back to the ground state, and part of the excess energy may be released and emitted as light. The emitted light is of lower energy, and of longer wavelength, than the absorbed light, thus the color of the light that is emitted is different from the color of the light that has been absorbed. De-excitation returns the fluorophore to its ground state. The fluorophore can absorb light energy again and go through the excited state to ground state process repeatedly.

Fluorescence Spectra

A fluorescent dye absorbs light over a range of wavelengths and every dye has a characteristic excitation range. This range of excitation wavelengths is referred to as the fluorescence excitation spectrum and reflects the range of possible excited states that the dye can achieve. Certain wavelengths within this range are more effective for excitation than other wavelengths. A fluorophore is excited most efficiently by light of a particular wavelength. This wavelength is the excitation maximum for the fluorophore. Less efficient excitation can occur at wavelengths near the excitation maximum; however, the intensity of the emitted fluorescence is reduced. Although illumination at the excitation maximum of the fluorophore produces the greatest fluorescence output, illumination at lower or higher wavelengths affects only the intensity of the emitted light; the range and overall shape of the emission profile are unchanged.

Fluorophore molecules, when excited, emit over a range of wavelengths. This range of wavelengths is referred to as the fluorescence emission spectrum. There is a spectrum of energy changes associated with these emission events. A molecule may emit at a different wavelength with each excitation event because of changes that can occur during the excited lifetime, but each emission will be within the fluorescence emission spectrum. Although the fluorophore molecules all emit the same intensity of light, the wavelengths, and therefore the colors of the emitted light, are not homogeneous. The emission maximum is the wavelength where the population of molecules fluoresces most intensely. The excited fluorophore can also emit light at wavelengths near the emission maximum. However, this light will be less intense.

The emission maximum for a given fluorophore is always at a longer wavelength (lower energy) than the excitation maximum. This difference between the excitation and emission maxima is called the Stokes shift. The magnitude of the Stokes shift is determined by the electronic structure of the fluorophore, and is characteristic of the fluorophore molecule. The Stokes shift is due to the fact that some of the energy of the excited fluorophore is lost through molecular vibrations that occur during the brief lifetime of the molecule's excited state. This energy is dissipated as heat to surrounding solvent molecules as they collide with the excited fluorophore.

Filters and Light Sources

Fluorescence requires a source of excitation energy. There are many light source options for fluorescence. Selecting the appropriate light source, and filters for both excitation and emission, can increase the sensitivity of signal detection.

Several types of light sources are used to excite fluorescent dyes. The most common sources used are broadband sources, such as, for example, mercury-arc and tungsten-halogen lamps. These lamps produce white light that has peaks of varying intensity across the spectrum. When using broadband white light sources it is necessary to filter the desired wavelengths needed for excitation; this is most often done using optical filters. Optical filters selectively allow light of certain wavelengths to pass while blocking out undesirable wavelengths. A bandpass excitation filter transmits a narrow range of wavelengths and may be used for selective excitation.

Laser excitation sources provide wavelength peaks that are well-defined, selective, and of high intensity allowing more selective illumination of the sample. The best performance is achieved when the dye's peak excitation wavelength is close to the wavelength of the laser. Several lasers commonly used include, for example, the compact violet 405 nm laser, 488 nm blue-green argon-ion laser, 543 nm helium-neon green laser, and 633 nm helium-neon red laser. Mixed-gas lasers such as, for example, the krypton-argon laser, can output multiple laser lines which may require optical filters to achieve selective excitation. High-output light-emitting diodes (LEDs) provide selective wavelengths, low cost and energy consumption, and long lifetime. Single-color LEDs are ideal for low-cost instrumentation where they can be combined with simple longpass filters that block the LED excitation and allows the transmission of the dye signal. However, the range of wavelengths emitted from each LED is still relatively broad and also may require the use of a filter to narrow the bandwidth.

Filters are important for selecting excitation wavelengths and for isolating the fluorescence emission emanating from the dye of interest. Stray light arising from sources other than the emitting fluorophores (for example, from the excitation source) interferes with the detection of the fluorescence emission. Stray light therefore must be contained to ensure only the fluorescence of the sample registers with the instrument's light-sensitive detectors. When a single dye is used, a long pass emission filter which selectively blocks out the excitation light to reduce background noise may be used to maximize the signal collected. If multiple dyes are used in the sample, a band pass emission filter can be used to isolate the emission from each dye.

Flow Cytometry

Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus.

Flow cytometry utilizes a beam of light (usually laser light) of a single wavelength that is directed onto a hydro-dynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analyzing fluctuations in brightness at each detector (usually one for each fluorescent emission peak) it then is possible to derive various types of information about the physical and chemical structure of each individual particle. FSC correlates with the cell volume and SSC depends on the inner complexity of the particle (i.e. shape of the nucleus, the amount and type of cytoplasmic granules or the membrane roughness).

Flow Cytometers

Flow cytometers are able to provide real-time analysis of several thousand particles every second and can actively separate and isolate particles having specified properties. Single-cell suspensions first must be prepared to analyze solid tissues.

A flow cytometer has five main components: 1) a flow cell where a liquid stream (sheath fluid) carries and aligns the cells so that they pass single file through the light beam for sensing; 2) a light source, such as lamps (mercury, xenon); high power water-cooled lasers (argon, krypton, dye laser); low power air-cooled lasers (argon (488 nm), red-HeNe (633 nm), green-HeNe, HeCd (UV)); or diode lasers (blue, green, red, violet); 3) a detector and Analogue to Digital Conversion (ADC) system for generating FSC and SSC as well as fluorescence signals; 4) an amplification system (linear or logarithmic): and 5) a computer for analysis of the signals.

Early flow cytometers were generally experimental devices, but recent technological advances have created a considerable market for the instrumentation, the reagents used, such as, for example, fluorescently-labeled antibodies, and analysis software. Modern instruments usually have multiple lasers and fluorescence detectors; up to 4 lasers and 18 fluorescence detectors within a single instrument are available. Increasing the number of lasers and detectors allows for multiple antibody labeling, and can identify a target population by its phenotype. Certain instruments can take digital images of individual cells more precisely, allowing for the analysis of fluorescent signal location within or on the surface of cells.

The use of fluorescent molecules, such as fluorophore-labeled antibodies, in flow cytometry is a common way to study cellular characteristics. Within these types of experiments, a labeled antibody is added to the cell sample. The antibody then binds to a specific molecule on the cell surface or inside the cell. Finally, when the laser light of the appropriate wavelength strikes the fluorophore, a fluorescent signal is emitted and detected by the flow cytometer.

The data generated by flow cytometers can be plotted in a single dimension, to produce a histogram, or in two dimensional dot plots or even in three dimensions. The regions on these plots can be sequentially separated, based on fluorescence intensity, by creating a series of subset extractions (referred to as "gates"). Specific gating protocols exist for diagnostic and clinical purposes especially in relation to hematology. The plots often are made on logarithmic scales. Signals at the detectors have to be compensated electronically as well as computationally due to emission spectra overlap of different fluorophores. Data accumulated using the flow cytometer may be exported to be re-analyzed elsewhere, freeing up the instrument for other researchers to use.

FACS

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell. It provides fast, objective and quantitative recording of fluorescent signals from individual cells as well as physical separation of cells of particular interest. The term "FACS" is not a generic term for flow cytometry, although many immunologists inappropriately use the term FACS for all types of sorting and non-sorting applications.

Utilizing FACS, a cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell being in a droplet. Before the stream breaks into droplets the flow passes through a fluorescence measuring station where the fluorescent character of interest of each cell is measured. An electrical charging ring or plane is placed just at the point where the stream breaks into droplets. A charge is placed on the ring based on the prior light scatter and fluorescence intensity measurements, and the opposite charge is trapped on the droplet as it breaks from the stream. The charged droplets then fall through an electrostatic deflection system that diverts droplets into containers based upon their charge. In some systems the charge is applied directly to the stream while a nearby plane or ring is held at ground potential and the droplet breaking off retains charge of the same sign as the stream. The stream is then returned to neutral after the droplet breaks off.

Fluorescence Detection

For proper data interpretation, the fluorescent light recorded from one fluorescent source must be distinguished from that recorded from other fluorescent sources. For that reason, the ideal fluorophore has a fluorescence emission profile of a very intense, narrow peak that is well separated from all other emission peaks. Typical organic dyes and fluorescent proteins, however, have broad emission peaks that may overlap, (i.e., emit some light in the same wavelength range). This spectral overlap may compromise data and analysis.

Multiple Fluorescent Signals

Background fluorescence, which may originate from endogenous sample constituents (autofluorescence) or from unbound or nonspecifically bound reagents, may severely compromise fluorescence detection. FIG. 2 shows fluorescence detection of mixed species. Excitation (EX) in overlapping absorption bands A1 and A2 produces two fluorescent species with spectra E1 and E2. The detection of autofluorescence (represented here by the A2-E2 spectra) can be minimized either by selecting filters that reduce the transmission of E2 relative to E1 or by selecting reagents that absorb and emit at longer wavelengths. Although narrowing the fluorescence detection bandwidth increases the resolution of E1 and E2, it also compromises the overall fluorescence intensity detected. Signal distortion caused by autofluorescence of cells, tissues and biological fluids is most readily minimized by using reagents that can be excited at >500 nm. At longer wavelengths, light scattering by dense media such as tissues is much reduced, resulting in greater penetration of the excitation light. The use of optical filters isolate quantitative emission signals S1 and S2.

Multicolor labeling incorporates the use of two or more probes to simultaneously monitor different biochemical functions. This technique has major applications in flow cytometry, DNA sequencing, fluorescence in situ hybridization and fluorescence microscopy. Signal isolation and data analysis are facilitated by maximizing the spectral separation of the multiple emissions (E1 and E2 in FIG. 2). Consequently, fluorophores with narrow spectral bandwidths, such as, for example, Alexa Fluor dyes and BODIPY dyes (Molecular Probes, Eugene, Oreg.), are useful in multicolor applications. An ideal combination of dyes for multicolor labeling would exhibit strong absorption at a coincident excitation wavelength and well-separated emission spectra (FIG. 2). Unfortunately, it is not simple to find single dyes with the requisite combination of a large extinction coefficient for absorption and a large Stokes shift.

Signal Amplification

Fluorescence signals may be amplified by increasing the number of fluorophores available for detection. However, simply increasing the probe concentration can be counterproductive and often produces marked changes in the probe's chemical and optical characteristics. The effective intracellular concentration of probes loaded by bulk permeabilization methods usually is much higher (>10-fold) than the extracellular incubation concentration. Additionally, the increased labeling of proteins or membranes ultimately leads to precipitation of the protein or gross changes in membrane permeability. Antibodies labeled with more than four to six fluorophores per protein may exhibit reduced specificity and reduced binding affinity. At high degrees of substitution, the extra fluorescence obtained per added fluorophore typically decreases due to self-quenching.

Compensation

The presence of multiple fluorescent signals must be accommodated within any fluorescence detection system for accurate quantification and analysis. Fluorescence is recorded using an emission filter chosen to collect the maximum amount of light coming from the fluorophore of interest and to exclude as much light as possible from other nearby fluorophores or fluorescent sources. While an emission filter efficiently captures the emission peak of the target fluorophore, it also may collect the light from one or more additional fluorophores due to spectral overlap in the emission profiles. The term "compensation" as used herein refers to correction of the emission signal to accurately estimate the fluorescence signal for a given fluorophore. A percentage of fluorescence is subtracted from one channel measuring a fluorophore from a second channel measuring the fluorescence of the second (or multiple) fluorophore such that the contribution of the incidental fluorescence is removed. Depending upon the instrument and software used, compensation may be set either in the instrument hardware before the sample is run or within the software after data collection. Every fluorophore combination that shows spectral overlap must be compensated. To determine the amount of compensation required to correct the fluorescence data, single-color samples (either aliquots of the cell sample stained with each fluorophore separately or microspheres that capture an individual reagent) are utilized and analyzed in parallel with the experimental samples stained with multiple fluorophores.

The complex methodologies involved in fluorescence and fluorescence detection provide significant hurdles for the researcher to consider. The further complexities of flow cytometry, combined with the consequent design of experimental protocol and detailed analysis involving numerous fluorophores and fluorescent signals, provide additional obstacles for the efficient utilization of flow cytometry. Proper consideration of spectral overlap that results from use or inclusion of multiple fluorescent materials in different detection systems currently is reactive to these problems as they arise.

There is a need in the art for identifying, important dye-detector spectral overlaps for use in designing flow cytometry experiments.

SUMMARY

This invention relates to the field of flow cytometry, more specifically a method of identifying important dye-detector spectral overlaps for use in designing flow cytometry experiments. According to one aspect, the present invention provides a method for quantifying the impact of spectral overlaps on dye selection and detector selection comprising: a) obtaining spectra of a dye; b) obtaining laser and optical filter configurations of a detector; c) obtaining a spectrum yield value; d) ranking the spectrum yield value; and e) quantifying the impact of spectral overlaps on dye selection and detector selection. In one embodiment, the spectra are excitation spectra. In another embodiment, the spectra are emission spectra. In another embodiment, the detector is a measurement channel of a flow cytometer. In another embodiment, the spectrum yield value is ranked as minimal. In another embodiment, the spectrum yield value is ranked substantial. In another embodiment, the spectrum yield value is obtained for a plurality of fluorophores. In another embodiment, the spectrum yield value is obtained for a plurality of detectors. In another embodiment, the plurality of detectors are obtained from a plurality of flow cytometers. In another embodiment, the dye is selected from the group comprising, of FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer AsRed2, mRFP1, HeRed1, monochlorobimane, calcein, the DyLight Fluors, cyanine, hydroxycoumarin, aminocoumarin, methoxycoumarin. Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof. In another embodiment, the method further comprises a computer.

In another aspect, the present invention provides a method for selecting dyes for use in flow cytometry comprising: a) obtaining spectra of a dye; b) obtaining laser and optical filter configurations for a detector; c) obtaining a spectrum yield value; d) ranking the spectrum yield value; e) selecting a dye based upon a spectrum yield value; and wherein the detector comprises a plurality of detectors, wherein the spectrum yield values are obtained from the dye and the plurality of detectors. In one embodiment, the spectra are excitation spectra. In another embodiment, the spectra are emission spectra. In another embodiment, the detector is from a flow cytometer. In another embodiment, the spectrum yield value is ranked as minimal. In another embodiment, the spectrum yield value is ranked as substantial. In another embodiment, the spectrum yield value is obtained for a plurality of dyes. In another embodiment, the dye is selected from the group comprising of FTC, R-phycoerythrin (PE), PE-Texas Red Tandem, PECy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1. ZsYellow1, DsRed2, DsRed monomer, AsRed2, mRFP1, HeRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof. In another embodiment, the method further comprises a computer.

In another aspect, the present invention provides a method for selecting a detector for use in flow cytometry comprising: a) obtaining spectra of at least one dye; b) obtaining laser and optical filter configurations from one or multiple detectors; c) obtaining spectrum yield values; d) ranking the spectrum yield values; e) selecting a detector based upon a spectrum yield values; wherein the detector comprises a plurality of detectors, and wherein spectrum yield values are obtained from the at least one dye and the plurality of detectors. In one embodiment, the spectra are excitation spectra. In another embodiment, the spectra are emission spectra. In another embodiment, the detector is a component of a flow cytometer. In another embodiment, the spectrum yield value is ranked as minimal. In another embodiment, the spectrum yield value is ranked as substantial. In another embodiment, the spectrum yield value is obtained for a plurality of dyes. In another embodiment, the spectrum yield value is obtained for a plurality of detectors. In another embodiment, the plurality of detectors are from a plurality of flow cytometers. In another embodiment, the dye is selected from the group comprising of FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1. ZsYellow1, DsRed2, DsRed monomer, AsRed2, mRFP1, HeRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof. In another embodiment, the method further comprises a computer.

In another aspect, the present invention provides a method for selecting a detector for use in flow cytometry comprising: (a) obtaining spectrum of at least one dye; (b) obtaining a laser and optical filter configurations from a detector; (c) obtaining a spectrum yield value; (d) ranking the spectrum yield value; (e) selecting a detector based upon maximum spectrum yield value in relation to the filter bandwidth, wherein the detector comprises a plurality of detectors, and wherein spectrum yield values are obtained from the at least one dye and the plurality of detectors. According to one embodiment, the spectrum is an excitation spectrum. According to another embodiment, the spectrum is an emission spectrum. According to another embodiment, the detector of step (b) is a component of a flow cytometer. According to another embodiment, the spectrum yield value in step (c) is obtained for a plurality of dyes. According to another embodiment, the spectrum yield value in step (c) is obtained for a plurality of detectors. According to another embodiment, the dye is selected from the group comprising of FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HeRed1, monochlorobimane, calcein, the DyLight Fluors, cyanine, hydroxycoumarin, aminocoumarin, methoxycoumarin, Cascade Blue, Lucifer Yellow, NBD, PECy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof. According to another embodiment, the method further comprises a computer.

In another aspect, the present invention provides a method for spectrum yield and overlap estimation comprising five steps. First, excitation and emission spectra for the dyes of interest are accumulated in a computable form. One skilled in the art will recognize the spectra for some dyes commonly used in flow cytometry are available in public databases. Second, accurate descriptions of the measurements supported on the available instruments are assembled. Typical configurations for common instruments are known, and these can be edited to account for, for example, but not limited to, filter differences and different laser options. Third, a selection of reagents and dyes is assembled, a spectral overlap analysis is performed, and a spectrum yield value for each dye on each available detector is determined. Fourth, a measurement channel is identified as the primary detector for each dye; this identification takes into account the filter bandwidth and the spectrum yield value. The spectrum yield value for that dye on all other detectors in relation to the spectrum yield value on the primary detector is then evaluated. Fifth, the data is displayed. In one embodiment, the data is displayed as a color-coded table of the spectrum yield values with separate sections for measurement channels that are and are not primary for one of the selected dyes. In another embodiment, the section of the table with channels that are not primary detectors for any of the currently selected dyes can be used to assist in minimizing potential spectral overlap problems when additional dyes are to be added to the reagent set.

BRIEF DESCRIPTION OF DRAWINGS

FIG. 8 shows a data table of the evaluation of the 9-dye reagent set applied to the configuration of the Flasher II Jet-in-air sorter instrument. The rows represent the 9 dyes, and the columns represent the measurement channels that are designed as primary detectors for these dyes (green cells). Substantial spectral overlaps (greater than 15% primary yield) are shaded yellow and minimal overlaps are shaded blue. The numbers in the cells are calculated spectrum yield values.

FIG. 11 shows an evaluation of the LSR-II Analyzer. Values for all channels in active (left) and spare (right) sections are represented in a data table. The left half of the table is the same as FIG. 10. The right half shows the evaluation for the measurement channels that are not designated as primary for any of the dyes. This information can be used to estimate spectral overlap difficulties that may arise in adding another dye to the existing set and to make an optimal choice for a new dye.

DETAILED DESCRIPTION

Figure 1:
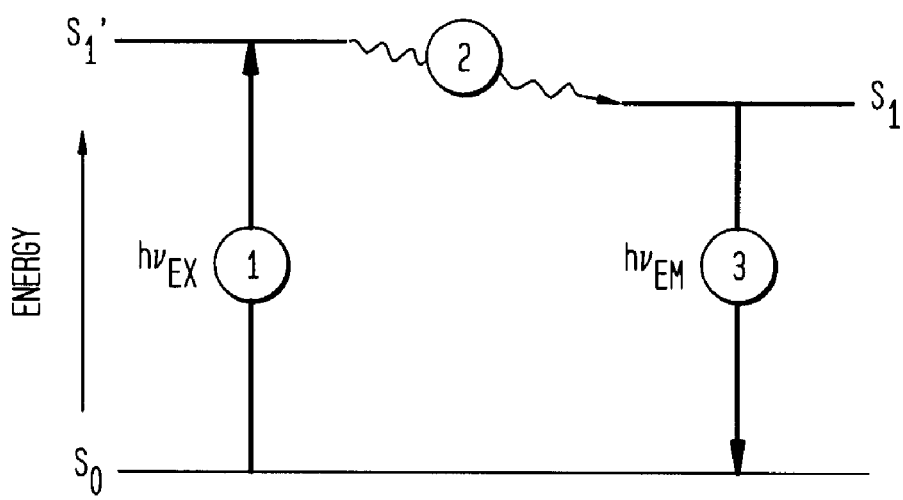
FIG. 1 shows a Jablonski diagram, which illustrates the process responsible for the fluorescence of fluorophores. Stage 1 encompasses excitation of the fluorophore from the ground state ($S_0$) to an excited state ($S_1$.) where the energy is partially dissipated, yielding a relaxed singlet excited state ($S_1$) from which fluorescence emission originates (Stage 2). Stage 3 represents the fluorescence emission.
Figure 2:
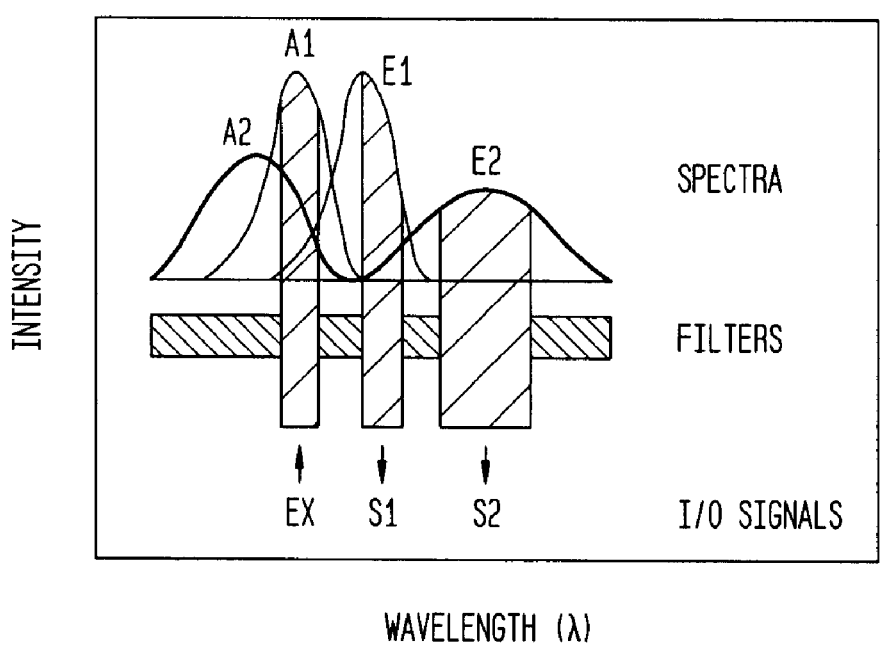
FIG. 2 shows fluorescence detection of mixed species. Excitation (EX) in overlapping absorption bands A1 and A2 produces two fluorescent species with spectra E1 and E2. Optical filters isolate quantitative emission signals S1 and S2.

The present invention provides methods for identifying important dye-detector spectral overlaps for use in designing flow cytometry experiments.

The term "cytometry" as used herein refers to a process in which physical and/or chemical characteristics of single cells, or by extension, of other biological or nonbiological particles in roughly the same size or stage are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and collect cells (or other small particles) with measured characteristics that fall within a user-selected range of values.

The term "fluorescent-activated cell sorting" (also referred to as "FACS"), as used herein refers to a method for sorting a heterogeneous mixture of biological cells into one or more containers, one cell at a time, based upon the specific light scattering and fluorescent characteristics of each cell.

The term "chromophore" as used herein refers to a part (or moiety) of a molecule responsible for its color. When a molecule absorbs certain wavelengths of visible light and transmits or reflects others, the molecule has a color. A chromophore is a region in a molecule where the energy difference between two different molecular orbitals falls within the range of the visible spectrum. Visible light that hits the chromophore thus can be absorbed by exciting an electron from its ground state into an excited state. In biological molecules that serve to capture or detect light energy, the chromophore is the moiety that causes a conformational change of the molecule when hit by light.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HeRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, Xrhodamine, Lissamine Rhodamine B, Texas Red, TruRed, and derivatives thereof.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light. FIG. 1 shows the Jablonski diagram which illustrates the process responsible for the fluorescence of fluorophores.

The term "excitation maximum" as used herein, refers to the specific wavelength for each fluorescent dye that most effectively induces fluorescence.

The term "excitation" as used herein may be represented by Equation 1:

$$S_0 + h\nu \rightarrow S_1 \quad \text{Equation [1]}$$

where h=Planck's constant and v=frequency of light (FIG. 1). A photon of energy ($h\nu_{EX}$) supplied by an external source, such as a laser or a lamp, is absorbed by the fluorophore creating an excited electronic singlet state ($S_1$). State $S_0$ is the ground state of the fluorophore and $S_1$ is its first (electronically) excited state. The excited state exists for a finite time during which the fluorophore undergoes conformational changes and is also subject to a multitude of possible interactions with its molecular environment. These processes have two important consequences: 1) the energy of $S_1'$ is partially dissipated, yielding a relaxed singlet excited state ($S_1$) from which fluorescence emission originates; and 2) not all the molecules initially excited by absorption return to the ground state ($S_0$) by fluorescence emission. Other processes, such as, but not limited to, collisional quenching or fluorescent resonance energy transfer (FRET), also may depopulate $S_1$.

Molecules in an excited state ($S_1$) can relax by various competing pathways. They can undergo 'non-radiative relaxation' in which the excitation energy is dissipated as heat (vibrations) to the solvent. Excited organic molecules can also relax via conversion to a triplet state which may subsequently relax via phosphorescence or by a secondary non-radiative relaxation step. The term "relax" as used herein refers to the energy loss of an excited molecule. Relaxation of an $S_1$ state can also occur through interaction with a second molecule through fluorescence quenching. The fluorescence quantum yield, which is the ratio of the number of fluorescence photons emitted to the number of photons absorbed, is a measure of the relative extent to which these processes occur.

The term "emission" as used herein may be represented by Equation 2:

$$S_1 \rightarrow S_0 + h\nu \quad \text{Equation [2]}$$

where h=Planck's constant and v=frequency of light (FIG. 1). A photon of energy ($h\nu_{EM}$) is emitted, returning the fluorophore to its ground state ($S_0$). Due to energy dissipation during the excited-state lifetime, the energy of this photon is lower, and therefore of longer wavelength, than the excitation photon ($h\nu_{EX}$). The difference in energy or wavelength represented by ($h\nu_{EX} - h\nu_{EM}$) is the Stokes shift. The Stokes shift allows emission photons to be detected against a low background, isolated from excitation photons.

The specific frequencies of exciting and emitted light are dependent on the particular system. The entire fluorescence process is cyclical. A single fluorophore may generate thousands of detectable photons. For polyatomic molecules in solution, the discrete electronic transitions represented by $h\nu_{EX} - h\nu_{EM}$ of FIG. 1 are replaced by rather broad energy spectra called the fluorescence excitation spectrum and the fluorescence emission spectrum, respectively. Generally, the fluorescence excitation spectrum of a single fluorophore species in dilute solution is identical to its absorption spectrum. Under the same conditions, the fluorescence emission spectrum is independent of the excitation wavelength, due to the partial dissipation of excitation energy during the excited-state lifetime. The emission intensity is proportional to the amplitude of the fluorescence excitation spectrum at the excitation wavelength.

The term "peak excitation" as used herein refers to the wavelength at the maximum of an excitation peak. The wavelength at the maximum of the excitation peak is the wavelength which induces the maximum excitation of a fluorophore.

Spectral overlaps among multiple dyes on different measurement channels (detectors) are important considerations in designing successful reagent combinations for multicolor flow cytometry experiments. The present invention provides methods for identifying the appropriate primary measurement channel for a given dye and for estimating the importance of spectral overlaps of that dye on other available measurement channels.

According to one aspect of the present invention, a method for quantifying the impact of spectral overlaps on dye selection and detector selection comprises the steps: a) obtaining a spectrum of a dye; b) obtaining a laser and optical filter configuration of a detector; c) obtaining a spectrum yield value; d) ranking the spectrum yield value; and e) quantifying the impact of spectral overlaps on dye selection and detector selection.

In one embodiment, the method comprises obtaining the excitation and emission spectra for a large number of dyes used in flow cytometry. As used herein, the term "spectra" (plural of "spectrum") refers to a range of light waves ordered in accordance with the magnitudes of their wavelengths. The term "emission spectrum" as used herein refers to the range of wavelengths an fluorophore emits light. Excitation and emission spectra of many dyes have been extensively studied. One skilled in the art will recognize that spectra may be obtained from the existing literature, or alternately, be determined via experimentation using various instrumentation such as, but not limited to, flow cytometers, fluorometers or spectrofluorometers. In another embodiment, the dyes are selected from dyes commonly used in flow cytometry. In another embodiment, the dyes are fluorophores.

In one embodiment, the spectrum is the excitation spectrum of the dye. In another embodiment, the spectrum is the emission spectrum of the dye.

In another embodiment, the detector is a component of a flow cytometer. Flow cytometers are commercially available from vendors such as, for example, BD Biosciences, Beckman Coulter, Partec, and Guava Technologies.

In another embodiment, the spectrum yield is ranked as minimal. In another embodiment the spectrum yield is ranked as substantial. As used herein, the term "ranked" refers to assignment of a relative position. As used herein, the term "substantial" refers to of ample or considerable amount, quantity, or size as determined by a user. As used herein, the term "minimal" refers to the least amount, quantity, or size possible as determined by a user. These designations generally refer to the impact a selected dye/detector combination may have upon the flexibility of the instant experimental protocol and of future, downstream experimental protocols. A user may arbitrarily assign these designations based upon the user's knowledge of the experimental protocol, instrumentation or reagents.

In another embodiment, the method comprises obtaining the excitation and emission spectra in a standard, computation compatible form. Such forms may include, but are not limited to, those compatible with CytoGenie™ software.

In another embodiment, the method further comprises a written description of the laser and optical filter configurations of a variety of flow cytometers that can be edited to describe particular instruments. One skilled in the art will recognize that written descriptions of laser and optical filter configurations of flow cytometers are easily obtained from the manufacturer, vendor, or sales representative or from individual observation of the instrument.

In another embodiment, the method further comprises selecting a set of dyes of interest and a particular instrument/configuration.

In another embodiment, the spectrum yield is evaluated for each dye/detector combination. As used herein, the term "spectrum yield" (or "spectrum yield value") refers to the percent of peak excitation at tile laser wavelength times the fraction of the emission spectrum within the detector pass band for each dye/detector combination. The spectrum yield is calculated from Equation 3:

$$SY = 100 * ((\text{excitation of dye at laser wavelength})/(\text{peak excitation of dye})) * ((\text{area of emission curve within detector filter band})/(\text{total area of emission curve}))$$

where SY=spectrum yield. In another embodiment, the spectrum yield value is expressed as an integer. In another embodiment, the spectrum yield value is expressed as a percentage of acceptability where acceptability equals 100. In another embodiment, the spectrum yield values are ranked to identify the probable primary measurement channel for each dye and to classify the spectral overlaps in other channels as either substantial or minimal. As used herein, the term "spectral overlap" refers to two or more light spectra with at least one common wavelength. As used herein, the terms "measurement channel" and "detector" are used interchangeably to refer to a component of a flow cytometer used to measure light. As used herein, the term "detector pass band" refers to an optical filter component of a detector of a flow cytometer located in the light path of incident light towards a detector. The determination of the spectrum yield value of each dye for each set of laser and optical filter configurations of various flow cytometers provides a quantitative ranking ability. This allows for the designation and highlighting of dye/channel combinations that may be appropriate, or alternately, problematic. In some embodiments, the ranking of the dye/channel combinations is presented by a computer software package.

In another embodiment, the measurements of multiple dyes on specific instruments are presented in comparison to the spectrum yield estimates for the same dyes and instruments to verify that the dye-detector rankings generally identify primary signal channels and substantial overlap/minimal overlap channels correctly.

In another embodiment, the estimates include more specific factors, such as, but not limited to, brightness of particular stains on particular cell populations. In another embodiment, the method evaluates the laser power and detector wavelength sensitivity. In another embodiment, the method provides reagent selection recommendations.

In another aspect, the present invention provides a method for selecting dyes for use in flow cytometry, the method comprising the steps: a) obtaining excitation and emission spectra of a dye; b) obtaining laser and filter configurations from a detector; c) obtaining a spectrum yield value; d) ranking the spectrum yield value; e) selecting a dye based upon a spectrum yield value; wherein the detector comprises a plurality of detectors, wherein spectrum yield values are obtained from the dye and the plurality of detectors.

In one embodiment, the spectrum is the excitation spectra of the dye. In another embodiment, the spectrum is the emission spectrum of the dye.

In another embodiment, the detector is a component of a flow cytometer. Flow cytometers are commercially available from vendors such as, for example, BD Biosciences, Beckman Coulter, Partec, and Guava Technologies.

In another embodiment, the spectrum yield is ranked as minimal. In another embodiment the spectrum yield is ranked as substantial. These designations generally refer to the impact a selected dye/detector combination may have upon the flexibility of the instant experimental protocol and of future, downstream experimental protocols. A user may arbitrarily assign these designations based upon the user's knowledge of the experimental protocol, instrumentation or reagents.

In one embodiment, the method comprises obtaining the excitation and emission spectra for a large number of dyes used in flow cytometry. One skilled in the art will recognize that spectra may be obtained from the existing literature, or alternately, be determined via experimentation using various instrumentation such as, but not limited to, flow cytometers, fluorometers or spectrofluorometers. In another embodiment, the dyes are selected from dyes commonly used in flow cytometry. In another embodiment, the dyes are fluorophores.

In another embodiment, the method comprises obtaining the excitation and emission spectra in a standard, computation compatible form. Such forms may include, but are not limited to, those compatible with CytoGenie™ software.

In another embodiment, the method further comprises written descriptions of laser and optical filter configurations of a variety of flow cytometers that can be edited to describe particular instruments. One skilled in the art will recognize that written descriptions of laser and optical filter configurations of flow cytometers are obtained from the manufacturer, vendor, or sales representative or from individual observation of the instrument.

In another embodiment, the method further comprises the step of selecting a set of dyes of interest and selecting a particular instrument/configuration.

In another embodiment, the spectrum yield is evaluated for each dye/detector combination. In another embodiment, the spectrum yield value is expressed as an integer. In another embodiment, the spectrum yield value is expressed as a percentage of acceptability where acceptability equals 100. In another embodiment, the spectrum yield values are ranked to identify the probable primary measurement channel for each dye and to classify the spectral overlaps in other channels as either substantial or minimal. The determination of the spectrum yield value of each dye for each set of laser and optical filter configurations of various flow cytometers provides a quantitative ranking ability, which allows for the designation and highlighting of dye/channel combinations that may be appropriate, or alternately, problematic. In some embodiments, the ranking of the dye/channel combinations is presented by a computer software package.

In another embodiment, the measurements of multiple dyes on specific instruments are presented in comparison to the spectrum yield estimates for the same dyes. Instruments verify that the dye-detector rankings generally identify primary signal channels and substantial overlap/minimal overlap channels correctly.

In another embodiment, the spectrum yield estimates include more specific factors, such as, but not limited to, brightness of particular stains on particular cell populations. In another embodiment, the method evaluates the laser power and detector wavelength sensitivity. In another embodiment, the method provides reagent selection recommendations.

In another aspect, the present invention provides a method for selecting a detector for use in flow cytometry, the method comprising the steps: a) obtaining spectrum of at least one dye; b) obtaining laser and optical filter configurations from a detector; c) obtaining a spectrum yield value; d) ranking the spectrum yield value; and e) selecting a detector based upon a spectrum yield value; wherein the detector comprises a plurality of detectors, and wherein spectrum yield values are obtained from the at least one dye and the plurality of detectors.

In one embodiment, the spectrum is the excitation spectrum of the dye. In another embodiment, the spectrum is the emission spectrum of the dye.

In another embodiment, the detector is a component of a flow cytometer. Flow cytometers are commercially available from vendors such as, for example, BD Biosciences, Beckman Coulter, Partec, and Guava Technologies.

In another embodiment, the spectrum yield is ranked as minimal. In another embodiment the spectrum yield is ranked as substantial. These designations generally refer to the impact a selected dye/detector combination may have upon the flexibility of the instant experimental protocol and of future, downstream experimental protocols. A user may arbitrarily assign these designations based upon the user's knowledge of the experimental protocol, instrumentation or reagents.

In one embodiment, the method comprises obtaining the excitation and emission spectra for a large number of dyes used in flow cytometry. One skilled in the art may recognize that spectra may be obtained from the existing literature, or alternately, may be determined via experimentation using various instrumentation such as, but not limited to, flow cytometers, fluorometers or spectrofluorometers. In another embodiment, the dyes are selected from dyes commonly used in flow cytometry. In another embodiment, the dyes are fluorophores.

In another embodiment, the method comprises obtaining the excitation and emission spectra in a standard, computation compatible form. Such forms may include, but are not limited to, those compatible with CytoGenie™ software.

In another embodiment, the method further comprises obtaining written descriptions of laser and optical filter configurations of a variety of flow cytometers that can be edited to describe particular instruments. One skilled in the art will that recognize written descriptions of laser and optical filter configurations of flow cytometers are easily obtained from the manufacturer, vendor, or sales representative or from individual observation of the instrument.

In another embodiment, the method further comprises the steps of selecting a set of dyes of interest and selecting a particular instrument/configuration.

In another embodiment, the spectrum yield is evaluated for each dye/detector combination. In another embodiment, the spectrum yield value is expressed as an integer. In another embodiment, the spectrum yield value is expressed as a percentage of acceptability where acceptability equals 100. In another embodiment, the spectrum yield values are ranked to identify the probable primary measurement channel for each dye and to classify the spectral overlaps in other channels as either substantial or minimal. The determination of the spectrum yield value of each dye for each set of laser and optical filter configurations of various flow cytometers provides a quantitative ranking ability. This allows for the designation and highlighting of dye/channel combinations that may be appropriate, or alternately, problematic. In some embodiments, the ranking of the dye/channel combinations is presented by a computer software package In another embodiment, the measurements or multiple dyes on specific instruments are presented in comparison to the spectrum yield estimates for the same dyes and instruments to verify that the dye-detector rankings generally identify primary signal channels and substantial overlap/minimal overlap channels correctly.

In another embodiment, the spectrum yield estimates include more specific factors, such as, but not limited to, brightness of particular stains on particular cell populations. In another embodiment, the method evaluates the laser power and detector wavelength sensitivity. In another embodiment, the method provides reagent selection recommendations.

In another aspect, the present invention provides a method for estimating spectrum yield and overlap estimation comprising five steps. First, excitation and emission spectra for the dyes of interest are accumulated in a computable form. One skilled in the art will recognize that the spectra for some dyes commonly used in flow cytometry are available in public databases.

Second, accurate descriptions of the measurements supported on the available instruments are assembled. Typical configurations for common instruments are known, and these can be edited to account for, for example, but not limited to, filter differences and different laser options. Third, a selection of reagents and dyes is assembled, a spectral overlap analysis is performed, and a spectrum yield value for each dye on each available channel is determined. Fourth, a measurement channel is identified as the primary detector for each dye; this identification takes into account the filter bandwidth and the spectrum yield value. The spectrum yield value for that dye on all other detectors in relation to the spectrum yield value on the primary detector then is evaluated. Fifth, the data is displayed. In one embodiment, the data is displayed as a color-coded table of the spectrum yield values with separate sections for measurement channels that are and are not primary for one of the selected dyes. In another embodiment, the section of the table with channels that are not primary detectors for any of the currently selected dyes can be used to assist in minimizing potential spectral overlap problems when additional dyes are to be added to the reagent set.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include the plural references unless the context clearly dictates otherwise. All technical and scientific terms used herein have the same meaning.

Publications discussed herein are provided solely for their disclosure prior to the filing date of the present application. Nothing herein is to be construed as an admission that the present invention is not entitled to antedate such publication by virtue of prior invention. Further, dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure the accuracy with respect to numbers used (e.g., amounts, temperature, etc.) but some experimental errors and deviations should be accounted for. (Unless indicated otherwise, parts are parts by weight, molecular weight is weight average molecular weight, temperature is in degrees Centigrade, and pressure is at or near atmospheric.

Example 1

This example illustrates quantitative scoring of dye/detector combinations. A nine dye reagent set, run on three different instruments, was utilized for spectral overlap evaluation. Spectrum yield tables were prepared for these dyes applied to the configuration description for each of the instruments.

Table 1 shows the compensation test samples for the comparison reagent set (all on reagent capture beads except monochlorobimane); controls included unstained cells, unstained reagent capture beads, and monochlorobiomane on cells.

TABLE 1

Compensation test samples for the comparison reagent set

| Dyes | Cell markers |
| --- | --- |
| Monochlorobiomane | cells |
| FITC | CD45 RO |
| PE | CD45 RA |
| PE-Cy5 | CD3 |
| PE-Cy55 | CD14 |
| PE-Cy7 | CD8 |
| APC | CD62L |
| AlexaFluor700 | CD1 1 a |
| APC-Cy7 | CD4 |

Figure 3:
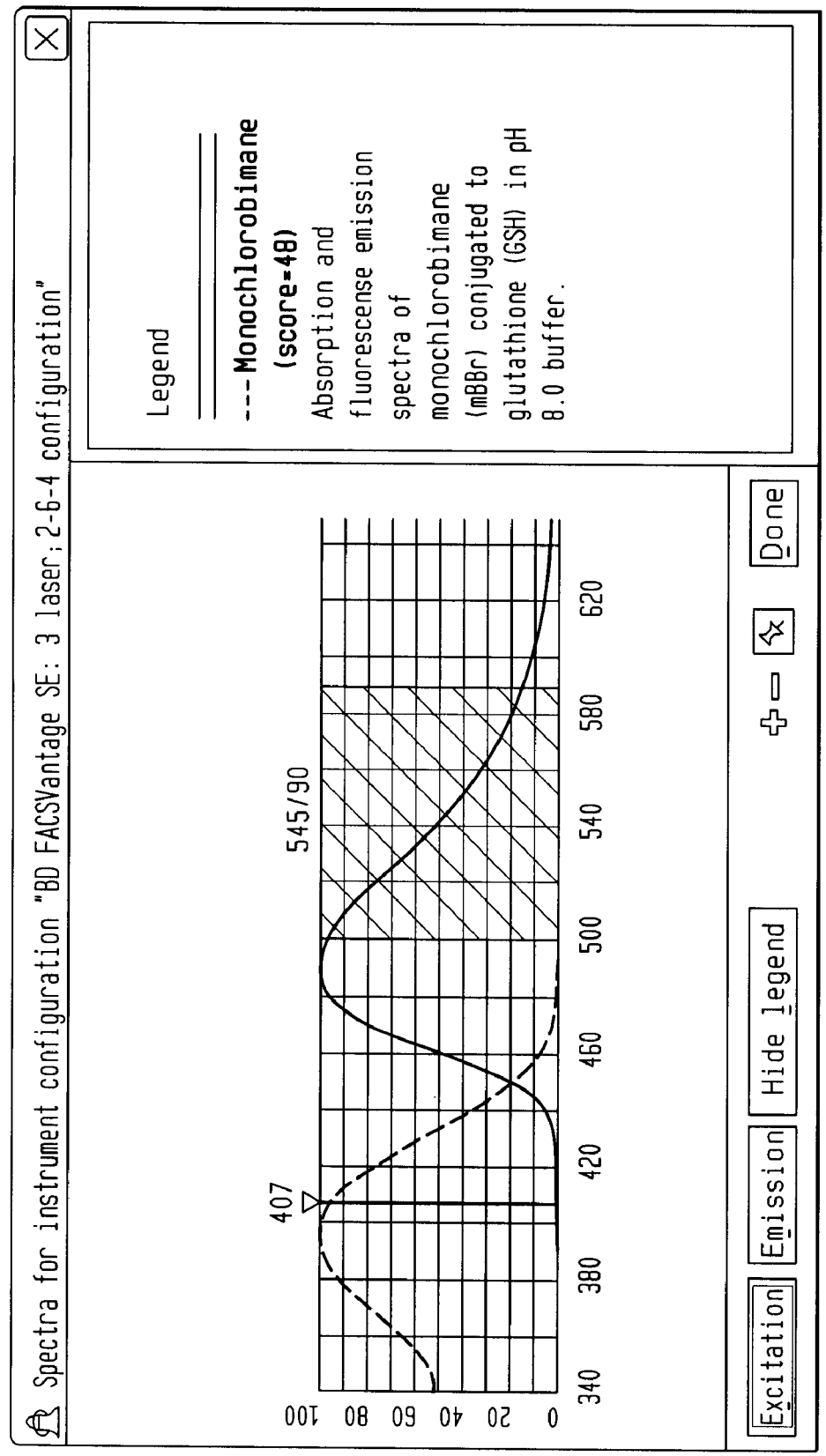
FIG. 3 shows a typical dye with a broad emission spectrum. The 407 nm laser is nearly ideal for excitation of this dye, and the 545/90 filter accepts about half of the total emission producing a spectrum yield score of 48 or 48% of what would be obtained with excitation at the peak and collection of all of the emission spectrum.

FIG. 3 shows spectra for monochlorobimane, a typical dye with a broad emission spectrum. The 407 nm laser is nearly ideal for excitation of this dye, and the 545/90 filter accepts about half of the total emission producing a spectrum yield score of 48 or 48% of what would be obtained with excitation at the peak and collection of all of the emission spectrum.

Figure 4:
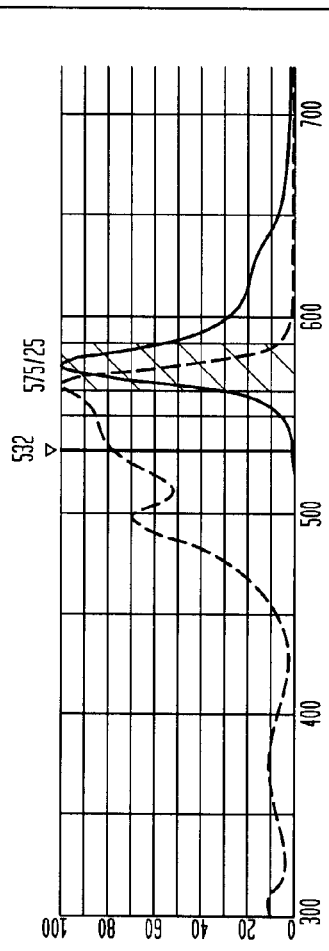
FIG. 4 shows PE spectrum with 532-575/25 detection. Phycoerythrin is excited at about 80% of peak efficiency at 532 nm, and the 575/25 filter is well placed in relation to the emission peak. R-PE has a score of 39 on 532-575/25. The detection score equals (excitation curve height at laser wavelength) divided by (excitation curve peak) multiplied by (emission curve area within filter) divided by (whole emission curve area); thus 39 equals 77 divided by 100 multiplied by 1879 divided by 3625.

FIG. 4 shows PE spectrum with 532-575/25 detection. Phycoerythrin is excited at about 80% of peak efficiency at 532 nm, and the 575/25 filter is well placed in relation to the emission peak. R-PE has a score of 39 on 532-575/25. A dye's highest score indicates the channel (laser/filter combination) with the most spectrum yield on this instrument. To determine the primary channel, the method also considers efficiency of yield by adjusting this score with the filter width. Combining different filters and/or lasers for this same dye can result in a higher value. If so then that channel is a better detector for this dye. The scales for the dyes are independent of each other. The detection score equals (excitation curve height at laser wave length) divided by (excitation curve peak) multiplied by (emission curve area within filter) divided by (whole emission curve area); thus 39 equals 77 divided by 100 multiplied by 1879 divided by 3625.

Figure 5:
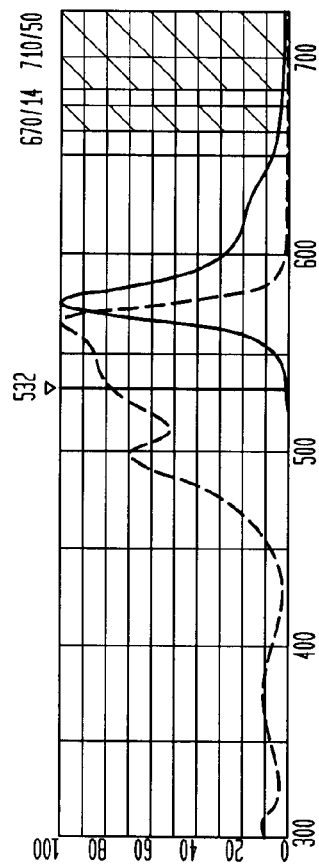
FIG. 5 shows PE has a small but not negligible spectrum yield even with emission filters at 670/14 (about 1%) and 710/50 (about 3% with a broad filter). R-PE has a score of 3 on 532-710/50; 3 equals 77 divided by 100 multiplied by 182 divided by 3635.

FIG. 5 shows PE has a small but not negligible spectrum yield even with emission filters at 670/14 (about 1%) and 710/50 (about 3% with this broad filter). R-PE has a score of 3 on 532-710/150; 3 equals 77 divided by 100 multiplied by 182 divided by 3635.

Figure 6:
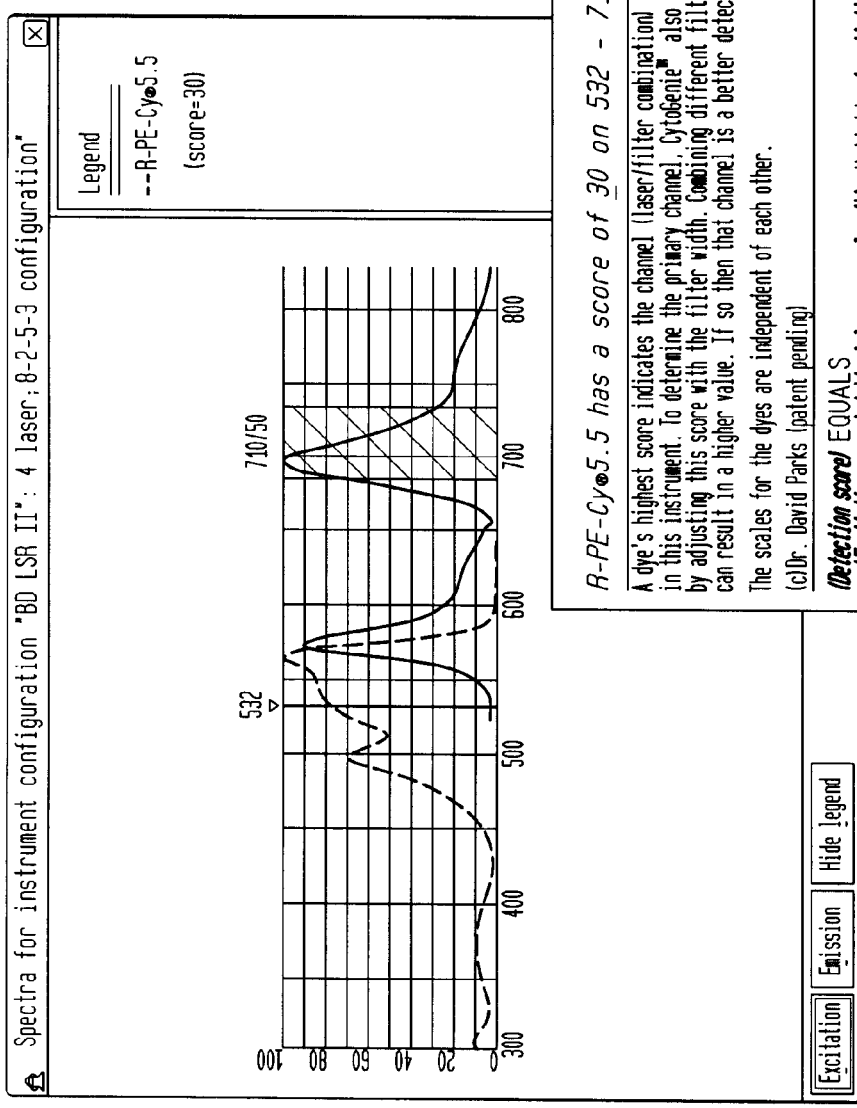
FIG. 6 shows tandem conjugate dyes like PE-Cy5.5 may present difficulties for spectrum yield evaluations since the PE to Cy5.5 ratio varies in different preparations, resulting in different amounts of direct fluorescence emission by the PE done (solid peak at 575 nm). Reagent deterioration may also lead to increases in this component of the emission. R-PE-Cy5.5 has a score of 30 on 532-710/50 (30 equals 77 divided by 100 multiplied by 3417 divided by 8644).

FIG. 6 shows tandem conjugate dyes like PE-Cy5.5 may present difficulties for spectrum yield evaluations since the PE to Cy5.5 ratio varies in different preparations, resulting in different amounts of direct fluorescence emission by the PE done (solid peak at 575 nm). Reagent deterioration may also lead to increases in this component of the emission. R-PE-Cy5.5 has a score of 30 on 532-710/50 (30 equals 77 divided by 100 multiplied by 3417 divided by 8644).

Figure 7:
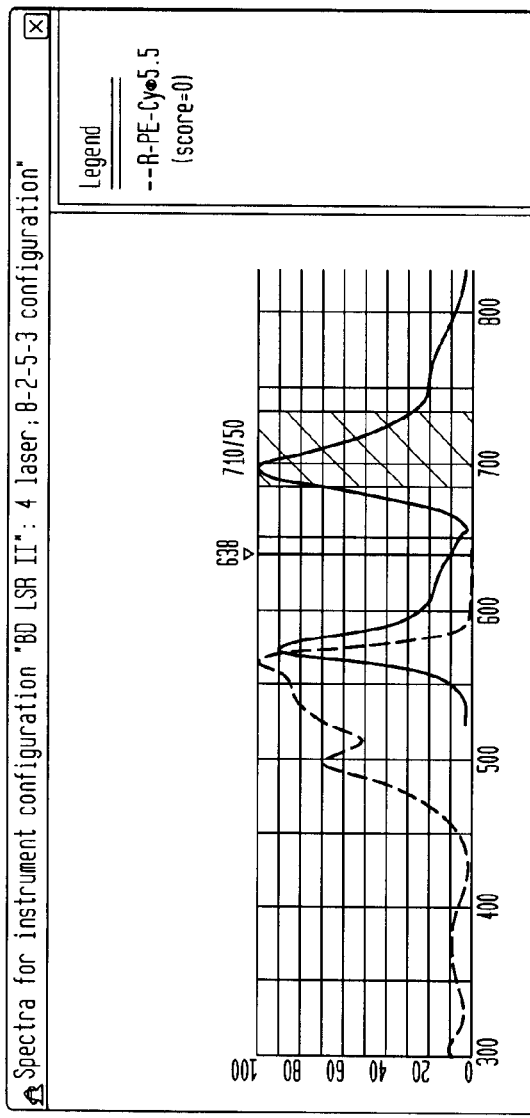
FIG. 7 shows how the complex structure of both the excitation and emission spectra of tandem conjugates may present difficulties when published spectra do not cover the full range of wavelengths. The excitation spectrum (dotted curve) was not extended to reveal the direct excitation of the Cy5.5 component at 638 nm. This led to an incorrect 0 score for a dye-channel combination that results in substantial actual signals. R-PE-Cy5.5 has a calculated score of 0 on 638710/50 (0 equals 0 divided by 100 multiplied by 3417 divided by 8644), but the actual excitation at 638 nm is not zero.

FIG. 7 shows how the complex structure of both the excitation and emission spectra of tandem conjugates may present difficulties when published spectra do not cover the full range of wavelengths. The excitation spectrum (dotted curve) was not extended to reveal the direct excitation of the Cy5.5 component at 638 nm. This led to an incorrect 0 score for a dye-channel combination that results in substantial actual signals. R-PE-Cy5.5 has a calculated score of 0 on 638 710/50

(0 equals 0 divided by 100 multiplied by 3417 divided by 8644), but the actual excitation at 638 nm is not zero.

FIG. 8 shows a data table of the evaluation of the 9-dye reagent set applied to the configuration of the Flasher II Jet-in-air sorter instrument. The rows represent the 9 dyes, and the columns represent the measurement channels that are designed as primary detectors for these dyes (green cells). Substantial spectral overlaps (greater than 15% primary yield) are shaded yellow and minimal overlaps are shaded blue. The numbers in the cells are calculated spectrum yield values.

Figure 9:
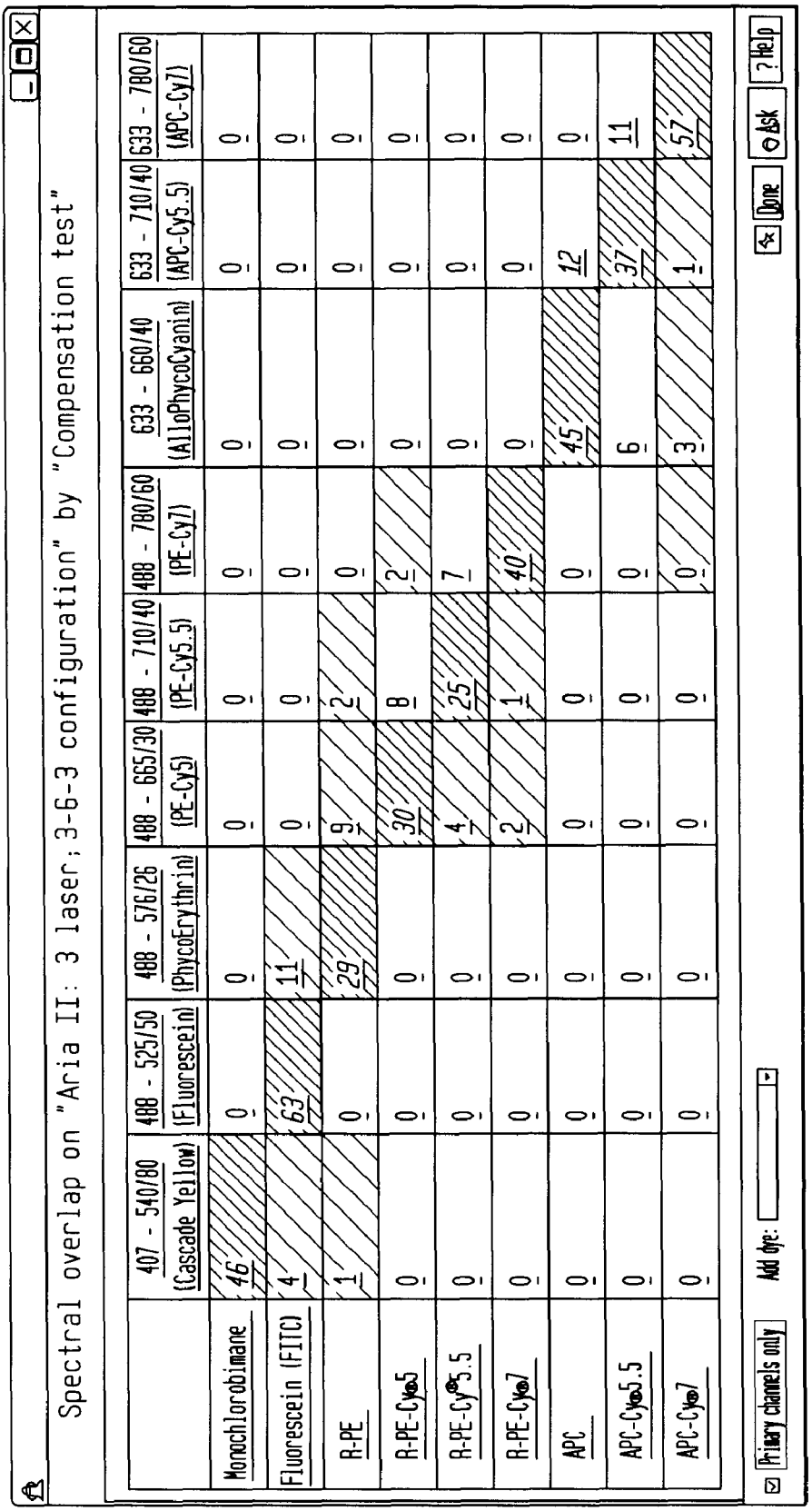
FIG. 9 shows an evaluation of the 9-dye reagent set applied to the configuration of the FACSAria instrument.

FIG. 9 shows an evaluation of the 9-dye reagent set applied to the configuration of the FACSAria instrument.

Figure 10:
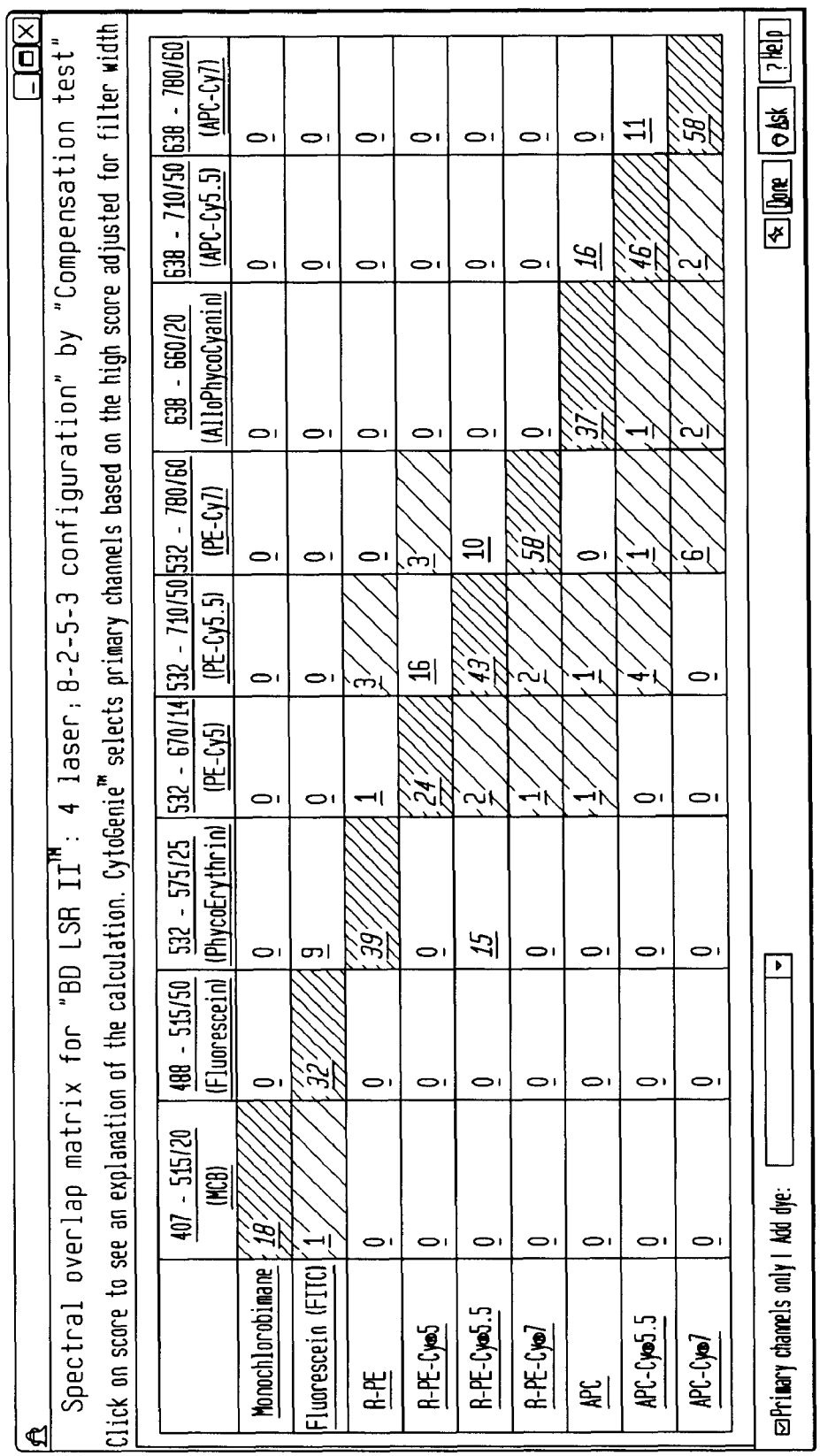
FIG. 10 shows an evaluation of the 9-dye reagent set applied to the configuration of the LSR-II analyzer.

FIG. 10 shows an evaluation of the 9-dye reagent set applied to the configuration of the LSR-II analyzer.

Figure 11:
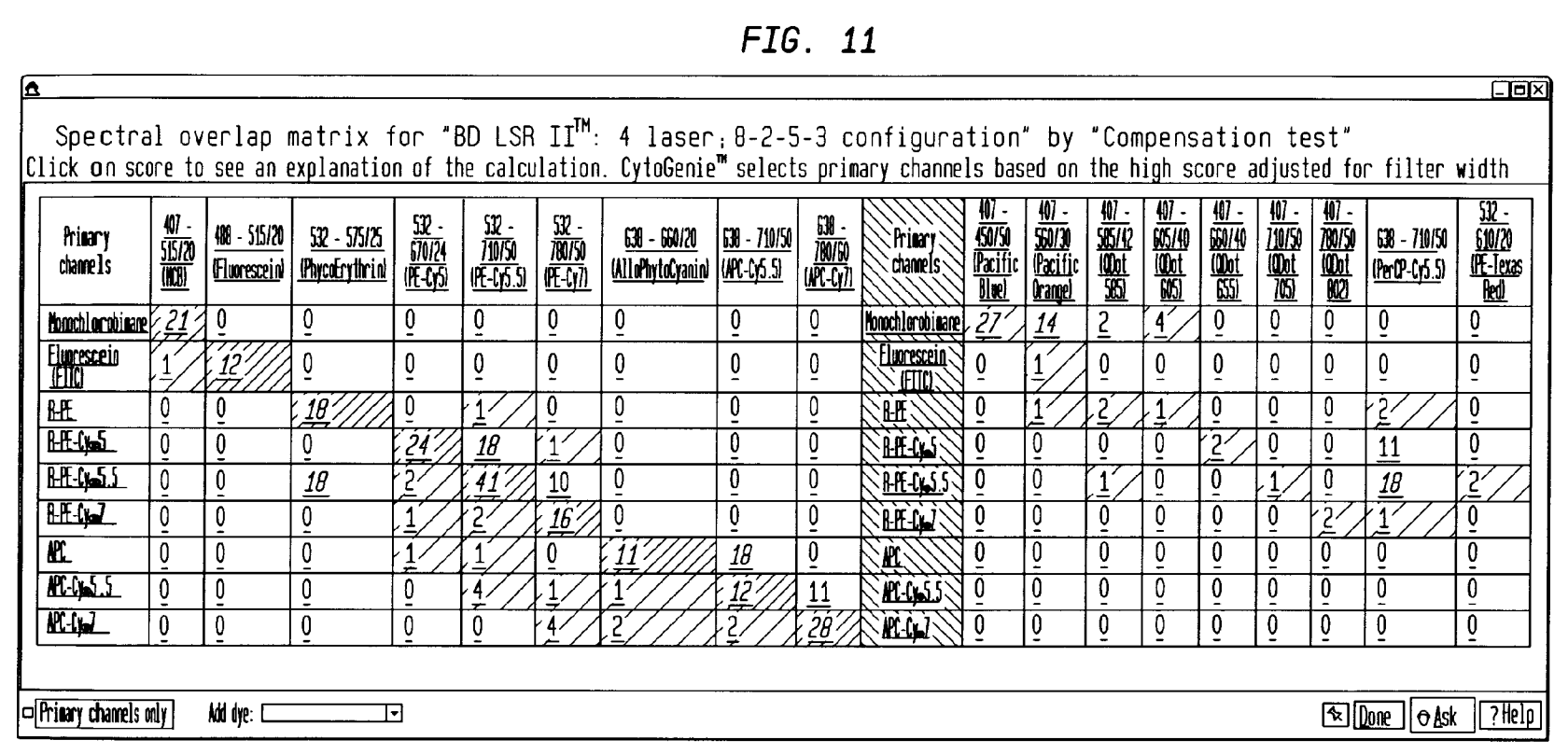

FIG. 11 shows an evaluation of the LSR-II Analyzer. Values for all channels in active (left) and spare (right) sections are represented in a data table. The left half of the table is the same as FIG. 10. The right half shows the evaluation for the measurement channels that are not designated as primary for any of the dyes. This information can be used to estimate spectral overlap difficulties that may arise in adding another dye to the existing set and to make an optimal choice for a new dye.

Figure 12:
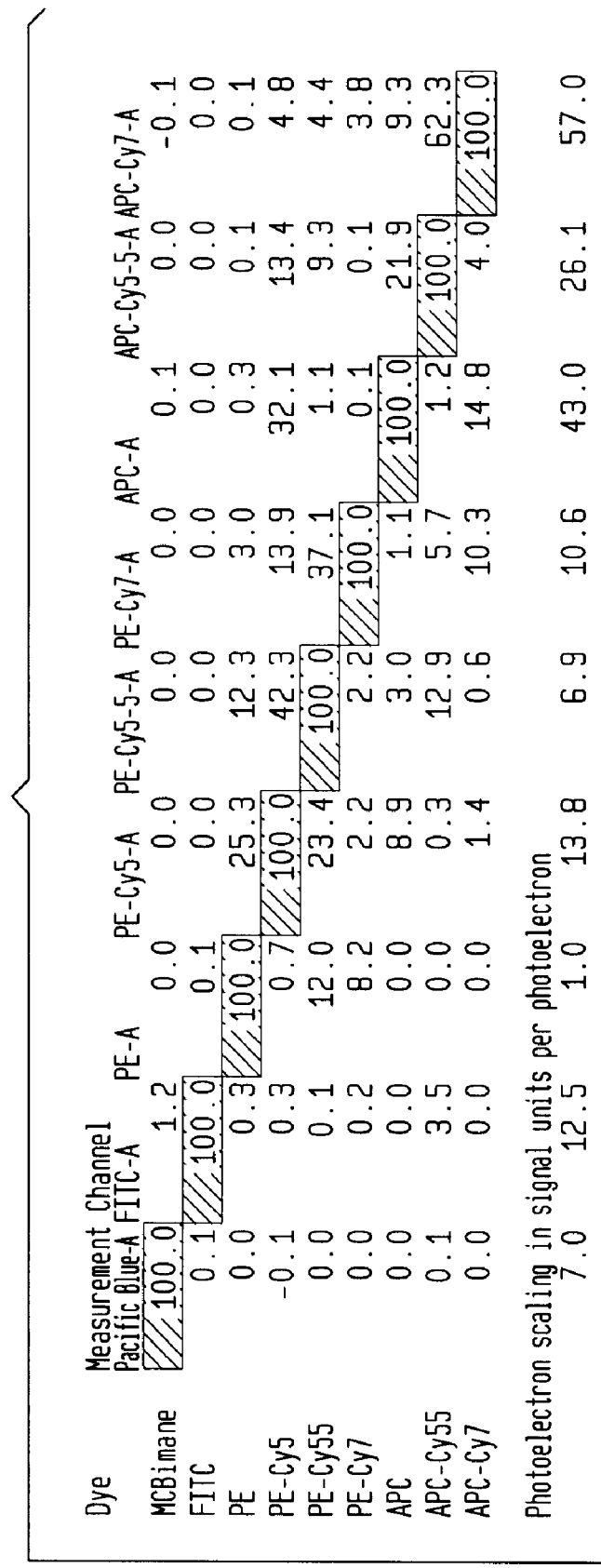
FIG. 12 shows LSR-II measurements for 9 single dye samples evaluated on 9 detectors and normalized to 100 in the primary channel for each dye (with photoelectron conversion values below). The effects of spectral overlaps on data quality are related to the number of photoelectrons that the overlap light signals generate in the non-primary detectors. To obtain an unbiased version of the spectral overlaps, the photoelectron scaling using uniform test particles with different fluorescence levels is estimated. The row of numbers below the main table shows the number of Diva signal units corresponding to one photoelectron on the 9 detectors under the conditions of the measurements.

FIG. 12 shows LSR-II measurements for 9 single dye samples evaluated on 9 detectors and normalized to 100 in the primary channel for each dye (with photoelectron conversion values below). The effects of spectral overlaps on data quality are related to the number of photoelectrons that the overlap light signals generate in the non-primary detectors. To obtain an unbiased version of the spectral overlaps, the photoelectron scaling using uniform test particles with different fluorescence levels is estimated. The row of numbers below the main table shows the number of Diva signal units corresponding to one photoelectron on the 9 detectors under the conditions of the measurements.

Figure 13:
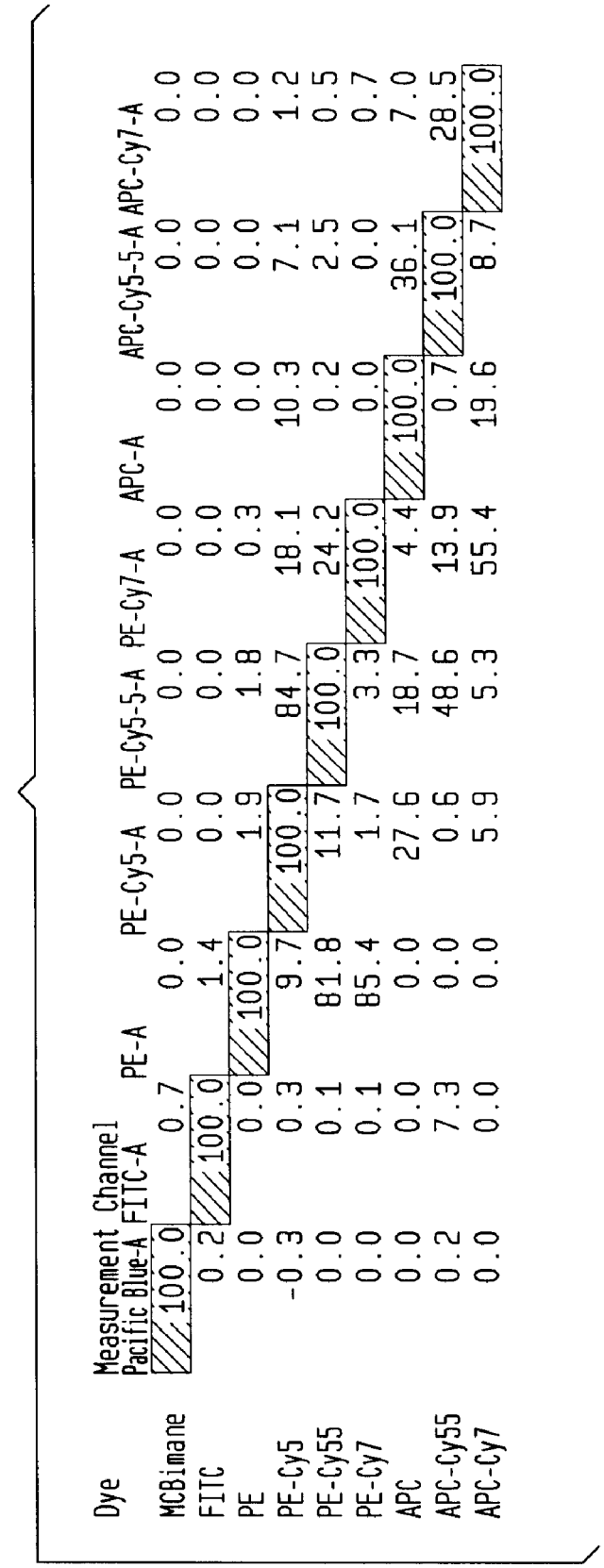
FIG. 13 shows the dye-channel spectral overlap data table adjusted for PMT gain differences and photoelectron scaling. After the initial adjustment, the primary channels were resealed to 100. In this embodiment, the spectral overlap table uses the photoelectron scale data to adjust for the different electronic gains of the measurement channels. Comparing to FIG. 12, more of the cells fall in the substantial overlap category. This is partially due to the inadequacies of the spectra used in the current testing and the large fraction of tandem reagents in the set. Some tandem reagent spectra may show best reagents rather than typical ones. The 7.3 yield for APC-Cy5.5 on the FITC measurement channel is anomalous and may represent contamination during reagent handling.

FIG. 13 shows the dye-channel spectral overlap data table adjusted for PMT gain differences and photoelectron scaling. After the initial adjustment, the primary channels were resealed to 100. In this embodiment, the spectral overlap table uses the photoelectron scale data to adjust for the different electronic gains of the measurement channels. Comparing to FIG. 12, more of the cells fall in the substantial overlap category. This is partially due to the inadequacies of the spectra used in the current testing and the large fraction of tandem reagents in the set. Some tandem reagent spectra may show best reagents rather than typical ones. The 7.3 yield for APC-Cy5.5 on the FITC measurement channel is anomalous and may represent contamination during reagent handling.

We claim:

1. A method for configuring a particle analysis mechanism by quantifying the impact of spectral overlaps on dye selection and detector selection comprising:
   (a) obtaining a spectrum of a dye,
   (b) obtaining a laser configuration and an optical filter configuration of a detector,
   (c) obtaining a spectrum yield value,
   (d) ranking the spectrum yield value,
   (e) quantifying the impact of spectral overlaps on dye selection and detector selection, and
   (f) configuring the particle analysis mechanism according to the results of the quantifying step.

2. The method according to claim 1, wherein the spectrum is an excitation spectrum.

3. The method according to claim 1, wherein the spectrum is an emission spectrum.

4. The method according to claim 1, wherein the detector of step (b) is a component of a flow cytometer.

5. The method according to claim 1, wherein the spectrum yield value is ranked in step (d) as minimal.

6. The method according to claim 1, wherein the spectrum yield value is ranked in step (d) as substantial.

7. The method according to claim 1, wherein the spectrum yield value in step (c) is obtained for a plurality of dyes.

8. The method according to claim 1, wherein the spectrum yield value in step (c) is obtained for a plurality of detectors.

9. The method according to claim 1, wherein the dye in step (a) is selected from the group consisting of fluorescein isothiocyanate, R-phycoerythrin, a tandem conjugate of sulforhodamine 101 acid chloride with R-phycoerythrin, a tandem conjugate of 1-(ε-carboxypentyl)-1'-ethyl-3,3,3',3'-tetramethylindodicarbocyanine -5,5'-disulfonate potassium salt N-hydroxysuccinimide ester with R-phycoerythrin, enhanced green fluorescent protein, enhanced yellow fluorescent protein, DsRed, allophycocyanin, peridinin chlorophyll protein, coumarin, 3-(εcarboxypentyl)-3'-ethyl-oxacarbocyanine-6,6'-disulfonate potassium salt N-hydroxysuccinimide ester, 1-(ε-carboxypentyl)-1'-ethyl-3,3,3',3'-tetramethylindocarbocyanine-5,5'-disulfonate potassium salt N-hydroxysuccinimide ester, 1-(ε-carboxypentyl)-1'-ethyl-3,3,3', 3'-tetramethyl-3H-benz(e)indocarbocyanine-5,5',7,7'-tetrasulfonate tripotassium salt N-hydroxysuccinimide ester, 1-(ε-carboxypentyl)-1'-ethyl-3,3,3',3'-tetramethylindodicarbocyanine-5,5'-disulfonate potassium salt N-hydroxysuccinimide ester, 1-(ε-carboxypentyl)-1'-ethyl-3,3,3',3'-tetramethyl -3H-benz(e)indocarbocyanine-5,5',7,7'-tetrasulfonate tripotassium salt N-hydroxysuccinimide ester, 1-(ε-carboxypentyl)-1'-ethyl-3,3,3',3'-tetramethylindodicarbocyanine -5,5'-disulfonate potassium salt N-hydroxysuccinimide ester, 2'-(4-ethoxyphenyl)-5-(4-methyl-1-piperazinyl)-5'-bi-1H-benzimidazole 2-[4-(aminoiminomethyl)phenyl]-1H-indole-6-carboximidamide, Phenol, 4-[5-(4-methyl-1-piperazinyl) [2,5'-bi-1H-benzimidazol]-2'-yl]-, trihydrochloride chromomycin A3, mithramycin, Quinolinium, 1,1-[1,3-propanediylbis[(dimethyliminio)-3,1-propanediyl]] bis[4-[(3-methyl-2(3H)- benzoxazolylidene)methyl]]-, tetraiodide, ethidium bromide, 7-aminoactinomycin D, acridine orange, Quinolinium, 1-1-[1,3-propanediylbis[(dimethyliminio)-3,1-propanediyl]]bis [4-[(3-methyl-2 (3H)-benzothiazolylidene)methyl]]-, tetraiodide, Quinolinium, 4-[(3-methyl-2(3H)-benzothiazolylidene) methyl]-1-[3-(3-(trimethylammonio)propyl]-, diiodide, quinolinium, 1-methyl-4-((3-methyl-2(3H)-benzothiazolylidene)methyl), salt with 4-methylbenzenesulfonic acid (1:1), Quinolinium, 1,1'-[1,3-propanediylbis [(dimethylminio)-3,1-propanediyl]]bis[4-[3-(3-methyl-2(3H)-benzothiazolylidene)-1-propenyl]-, tetraiodide, Quinolinium, 4-[3-(3-methyl-2 (3H)-benzothiazolylidene)-1-propenyl]-1-[3-(trimethylammonio) propyl]-, diiodide, propidium iodide, LDS 751, 2-[4-[bis(carboxymethyl)amino]-3-[2-[2-[bis(carboxymethyl)amino]-5-methylphenoxy]ethoxy]phenyl]-1H-indole-6-carboxylic acid, N-[2-[2-[2-[bis(carboxymethyl)amino]-5-(2,7-dichloro-6-hydroxy-3-oxo-3H-xanthen-9-yl)phenoxy]ethoxy]-4-methylphenyl]-N-(carboxymethyl)-glycine, dichlorodihydrofluorescein diacetate, dihydrorhodamine SNARF, Y66F, Y66H, enhanced blue fluorescent protein, green fluorescent protein uv, enhanced cyan fluorescent protein, green fluorescent protein, AmCyan1, Y77W, S65A, S65C, S65L, S65T, ZsGreen1, ZsYellow1, DsRed2, DsRed monomer, AsRed2, mRFP1, HcRed1, monochlorobimane, calcein, cyanine, hydroxycoumarin, aminocoumarin, methoxycoumarin, acetic acid, [(3,6,8-trisulfo-1-pyrenyl) oxy]-, 1-hydrazide, trisodium salt, 1H-Benz[de]isoquinoline-5,8-disulfonic acid, 6-amino-2-[(hydrazinocarbonyl) amino]-2,3-dihydro-1,3-dioxo-, dilithium salt, 6-[(7-nitro-2,1,3-benzoxadiazol-4-yl)amino]-hexanoic acid, conjugates of 1-(ϵ-carboxypentyl) -1'-ethyl-3,3,3',3'-tetramethylindotricarbocyanine-5,5'-disulfonate potassium salt N-hydroxysuccinimide ester with R-phycoerythrin, conjugates of allophycocyanin with 1-(ϵ-carboxypentyl)-1'-ethyl-3,3,3',3'-tetramethylindotricarbocyanine-5, 5'-disulfonate potassium salt N-hydroxysuccinimide ester, Red 613, fluorescein, 6-(5- and 6-fluoresceinyl-carboxamido)-hexanoic acid N-hydroxysuccinimide ester, 4,4-difluoro-5,7-dimethyl-4-bora-3a,4a-diaza-s-indacene-3-propionic acid, tetramethylrhodamine-6-isothiocyanate, X-rhodamine, lissamine rhodamine B, sulforhodamine 101 acid chloride, conjugate of peridinin chlorophyll protein with 1-(ϵ-carboxypentyl) -1'-ethyl-3,3,3',3'-tetramethyl-3H-benz(e)indodicarbocyanine-5,5',7,7'-tetrasulfonate tripotassium salt N-hydroxysuccinimide este, and fluorescent derivatives thereof.

10. The method according to claim 1, further comprising performing at least quantifying step (e) on a computer programmed with software to perform the quantifying step.

11. The method according to claim 1, wherein the dye in step (a) comprises a compound selected from the group consisting of

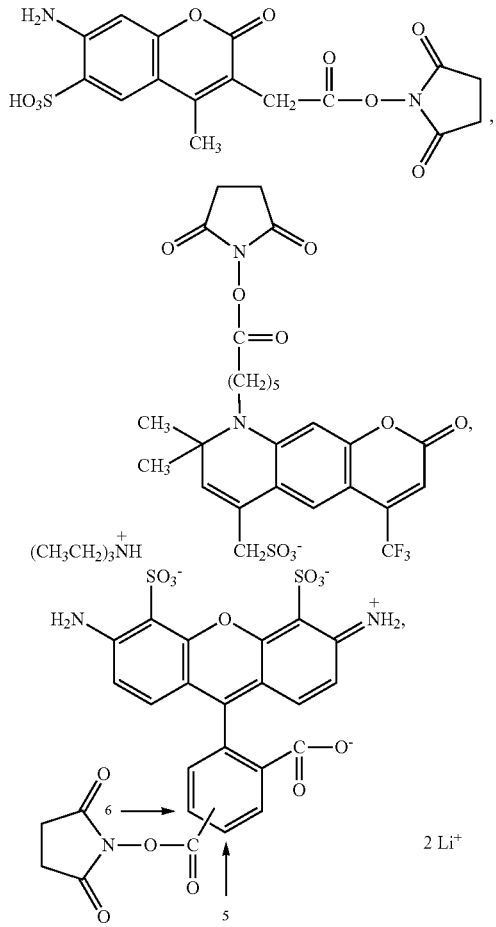

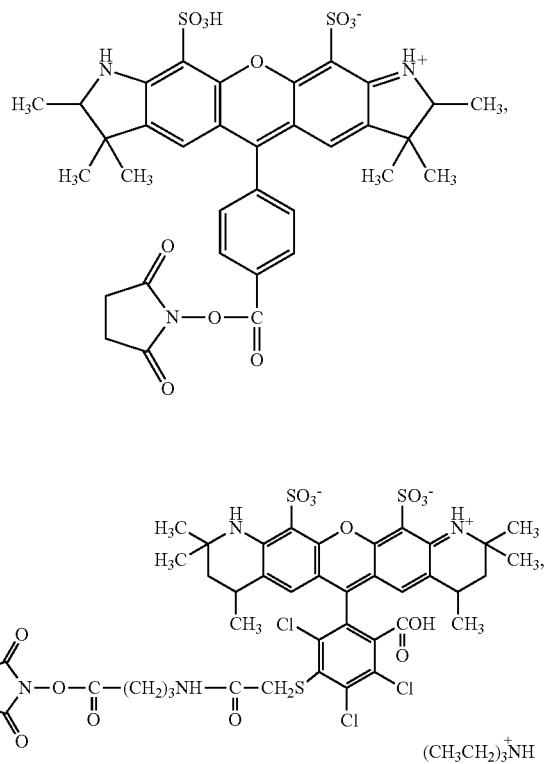

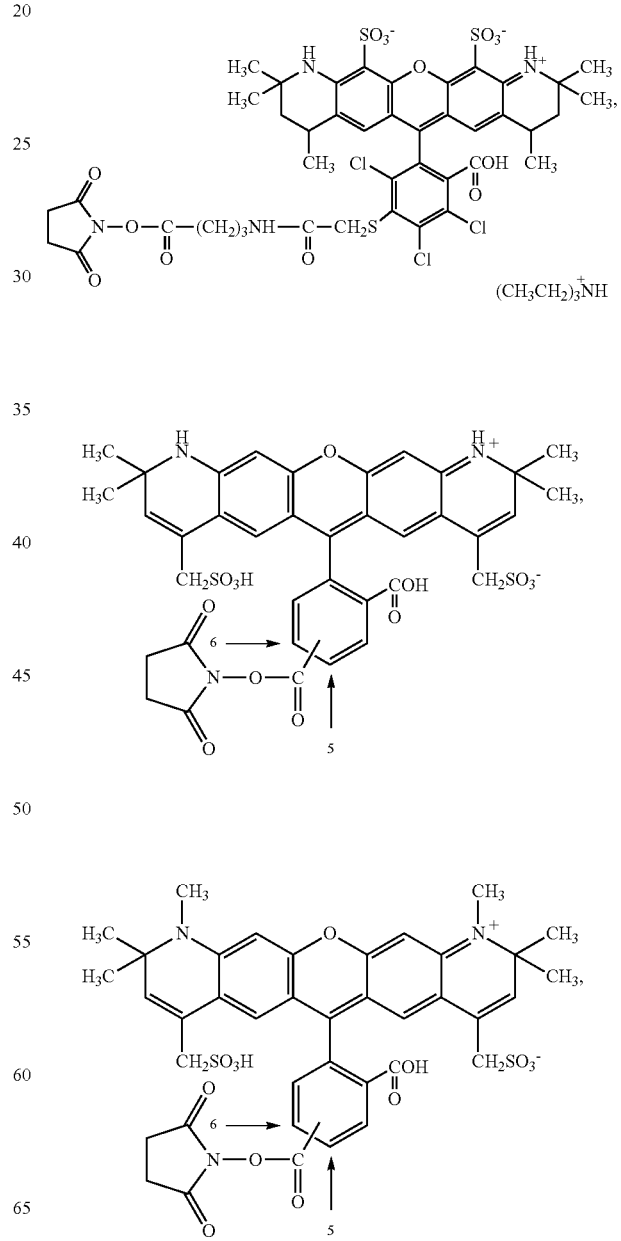

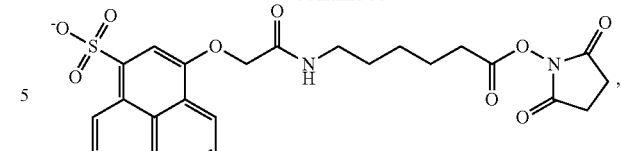

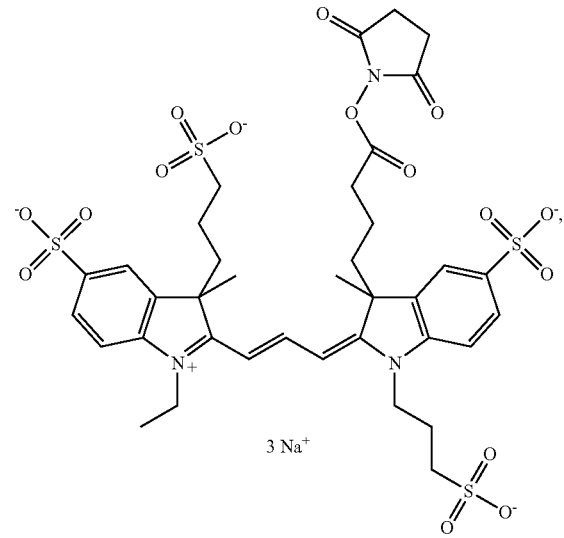

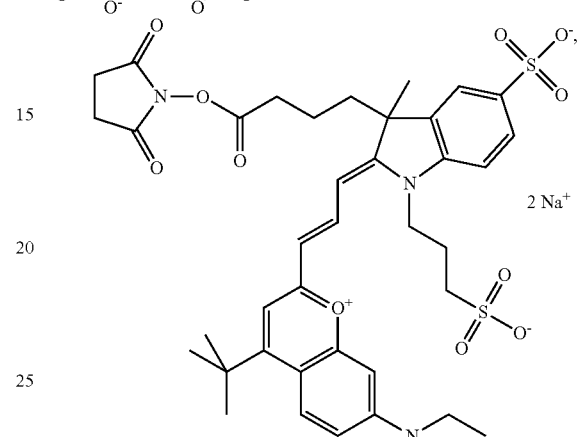

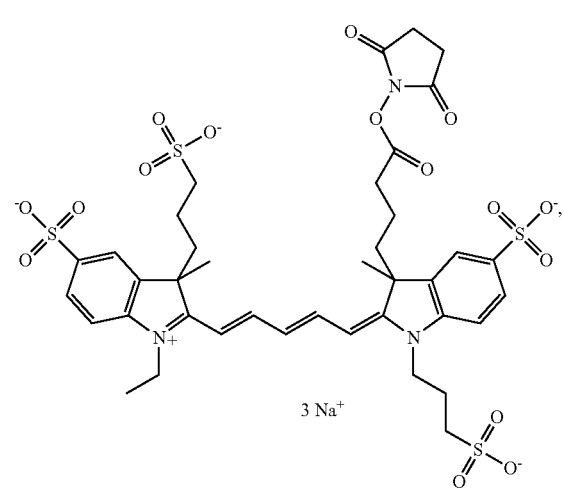

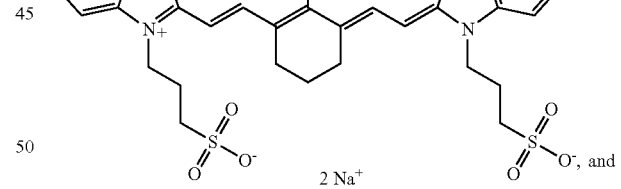

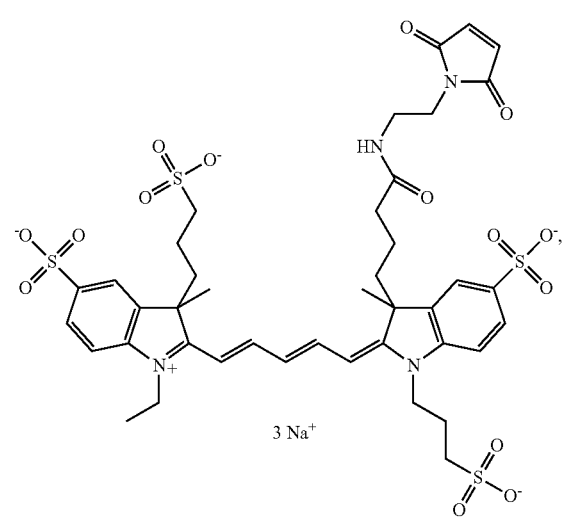

fluorescent derivatives thereof.

12. A method for selecting dyes for use in flow cytometry comprising:
 (a) obtaining a spectrum for each of a plurality of dyes in a form capable of being operated on by a digital computing device,
 (b) obtaining a laser and optical filter detector configuration for at least one detector in a form capable of being operated on by a digital computing device,
 (c) obtaining, via a digital computing device, for each of a plurality of combinations of a dye and a detector configuration for the at least one detector, a spectrum yield value,
 (d) ranking the spectrum yield values, (e) selecting a dye based upon the ranking of the spectrum yield values in step (d).

13. The method according to claim 12, wherein the spectrum is an excitation spectrum.

14. The method according to claim 12, wherein the spectrum is an emission spectrum.

15. The method according to claim 12, wherein the detector of step (b) is a component of a flow cytometer.

16. The method according to claim 12, wherein the spectrum yield value is ranked in step (d) as minimal.

17. The method according to claim 12, wherein the spectrum yield value is ranked in step (d) as substantial.

18. The method according to claim 12, wherein the spectrum yield value in step (c) is obtained for a plurality of dyes.

19. The method according to claim 12, wherein the dye in step (a) is selected from the group consisting of fluorescein isothiocyanate, R-phycoerythrin, a tandem conjugate of sulforhodamine 101 acid chloride with R-phycoerythrin, a tandem conjugate of 1-(ϵ-carboxypentyl)-1'-ethyl-3,3,3',3'-tetramethylindodicarbocyanine-5,5'-disulfonate potassium salt N-hydroxysuccinimide ester with R-phycoerythrin, enhanced green fluorescent protein, enhanced yellow fluorescent protein, DsRed, allophycocyanin, peridinin chlorophyll protein, coumarin, 3-(ϵ-carboxypentyl)-3'-ethyl-oxacarbocyanine-6,6'-disulfonate potassium salt N-hydroxysuccinimide ester, 1-(ϵ-carboxypentyl)-1'-ethyl-3,3,3',3'-tetramethylindocarbocyanine-5,5'-disulfonate potassium salt N-hydroxysuccinimide ester, 1-(ϵ-carboxypentyl)-1'-ethyl-3,3,3',3'-tetramethyl-3H-benz(e)indocarbocyanine-5,5',7,7'-tetrasulfonate tripotassium salt N-hydroxysuccinimide ester 1-(ϵ-carboxypentyl)-1'-ethyl-3,3,3',3'-tetramethylindodicarbocyanine-5,5'-disulfonate potassium salt N-hydroxysuccinimide ester, 1-(ϵ-carboxypentyl)-1'-ethyl-3,3,3',3'-tetramethyl-3H-benz(e)indocarbocyanine-5,5',7,7'-tetrasulfonate tripotassium salt N-hydroxysuccinimide ester, 1-(ϵ-carboxypentyl)-1'-ethyl-3,3,3',3'-tetramethylindotricarbocyanine-5, 5'-disulfonate potassium salt N-hydroxysuccinimide ester, 2'-(4-ethoxyphenyl)-5-(4-methyl-1-piperazinyl)-5'-bi-1H-benzimidazole, 2-[4-(aminoiminomethyl)phenyl]1-1H-indole-6-carboximidamide, Phenol, 4-[5-(4-methyl-1-piperazinyl)[2,5'-bi-1H-benzimidazo]-2'-yl]-, trihydrochloride chromomycin A3, mithramycin, Quinolinium, 1,1-[1,3-propanediylbis[(dimethyliminio)-3,1-propanediyl ]]bis[4-[(3-methyl-2(3H)-benzoxazolylidene)methyl]]-, tetraiodide, ethidium bromide, 7-aminoactinomycin D, acridine orange, Quinolinium, 1-1-[1,3- propanediylbis[(dimethyliminio)-3,1-propanediyl]]bis [4-(3-methyl-2(3H)-benzothiazolylidene)methyl]]-, tetraiodide, Quinolinium, 4-[(3-methyl-2(3H)-benzothiazolylidene) methyl]-1-[3-(trimethylammonio)propyl]-, diiodide, quinolinium, 1-methyl-4-((3-methyl-2(3H)-benzothiazolylidene)methyl), salt with 4-methylbenzenesulfonic acid (1:1), Quinolinium, 1,1'-[1,3-propanediylbis [(dimethylminio)-3,1-propanediyl]]bis[4-3-(3-methyl-2(3H)-benzothiazolylidene)-1-propenyl]-, tetraiodide, Quinolinium, 4-[3-(3-methyl-2(3H)-benzothiazolylidene)-1-propenyl]-1-[3-(trimethylammonio) propyl]-, diiodide, propidium iodide, LDS 751, 2-[4-[bis(carboxymethyl)amino]-3-[2-[2-[bis(carboxymethyl)amin]-5-methylphenoxy]ethoxy]phenyl]-1H-indole-6-carboxylic acid, N-[2-[2-[2-[bis (carboxymethyl)amino]-5-(2,7-dichloro-6-hydroxy-3-oxo-3H-xanthen-9-yl) phenoxy] ethoxy]-4-methylphenyl]-N-(carboxymethyl)-glycine, dichlorodihydrofluorescein diacetate, dihydrorhodamine, SNARF, Y66F, Y66H, enhanced blue fluorescent protein, green fluorescent protein uv, enhanced cyan fluorescent protein, green fluorescent protein, AmCyan1, Y77W, S65A, S65C, S65L, S65T, ZsGreen1, ZsYellow1, DsRed2, DsRed monomer, AsRed2, mRFP1, HcRed1, monochlorobimane, calcein, cyanine, hydroxycoumarin, aminocoumarin, methoxycoumarin, acetic acid, [(3,6,8-trisulfo-1-pyrenyl)oxy]-, 1-hydrazide, trisodium salt, 1H-Benz[de]isoquinoline-5,8-disulfonic acid, 6-amino-2-[(hydrazinocarbonyl) amino]-2,3-dihydro-1,3-dioxo-, dilithium salt, 6-[(7-nitro-2, 1,3-benzoxadiazol-4-yl)amino]-hexanoic acid, conjugates of 1-(ϵ-carboxypentyl) -1'-ethyl-3,3,3',3'-tetramethylindotricarbocyanine-5,5'-disulfonate potassium salt N-hydroxysuccinimide ester with R-phycoerythrin, conjugates of allophycocyanin with 1-(ϵ-carboxypentyl)-1'-ethyl-3,3,3',3'-tetramethylindotricarbocyanine-5, 5'-disulfonate potassium salt N-hydroxysuccinimide ester, Red 613, fluorescein, 6-(5-and 6-fluoresceinyl-carboxamido)-hexanoic acid N- hydroxysuccinimide ester, 4,4-difluoro-5,7-dimethyl-4-bora-3a,4a-diaza-s-indacene-3-propionic acid, tetramethylrhodamine-6-isothiocyanate, X-rhodamine, lissamine rhodamine B, sulforhodamine 101 acid chloride, conjugate of peridinin chlorophyll protein with 1-(ϵ-carboxypentyl)-1'-ethyl-3,3,3',3'-tetramethyl-3H-benz(e) indodicarbocyanine-5,5',7,7'-tetrasulfonate tripotassium salt N-hydroxysuccinimide ester, and fluorescent derivatives thereof.

20. The method according to claim 12, wherein the dye in step (a) comprises a compound selected from the group consisting of

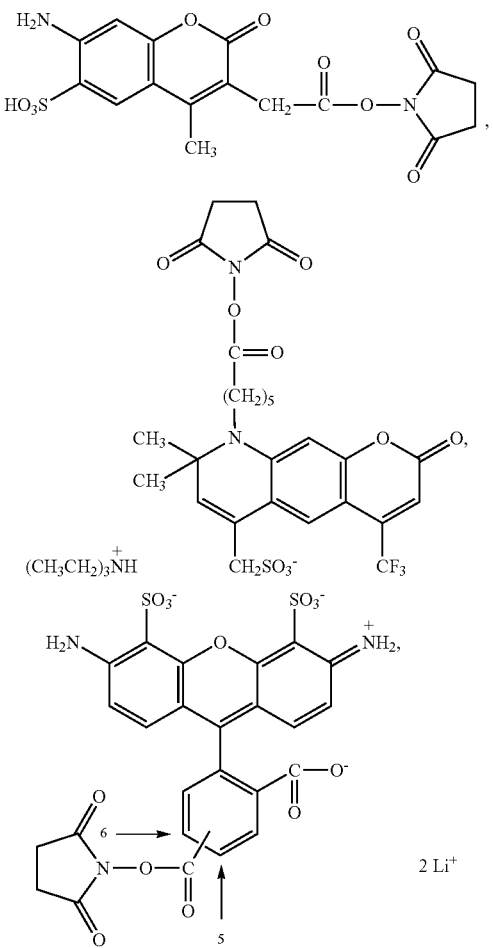

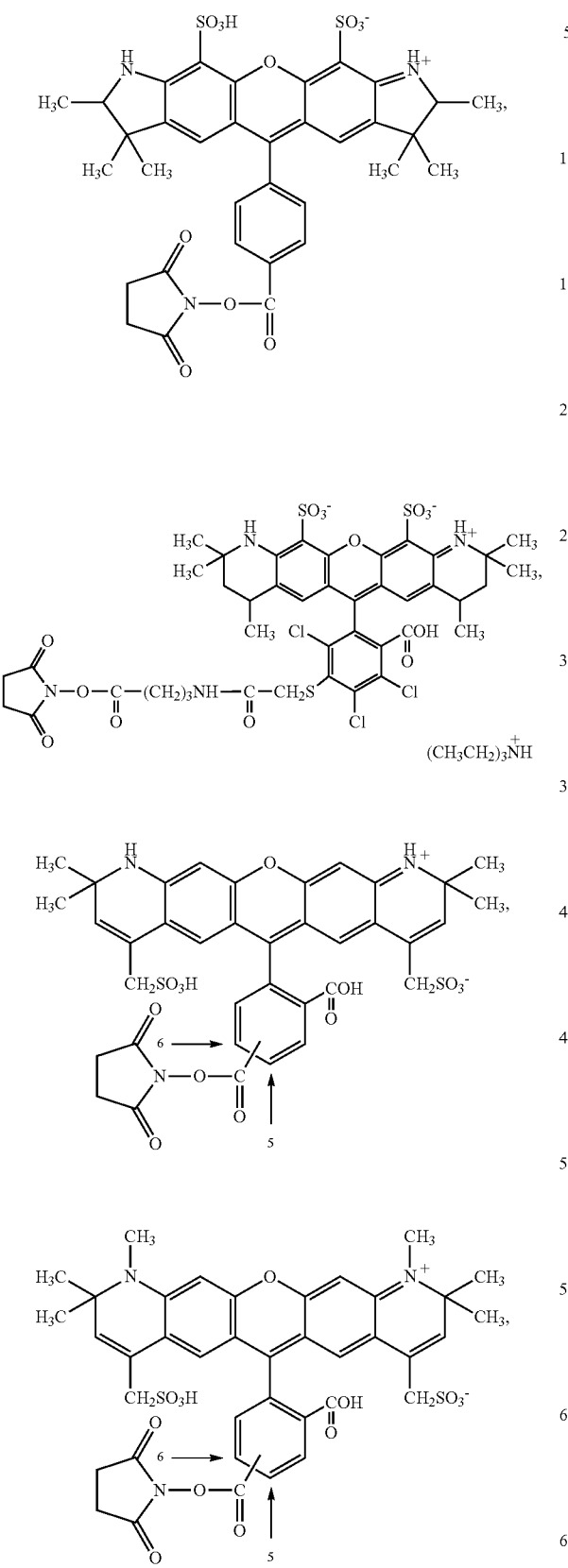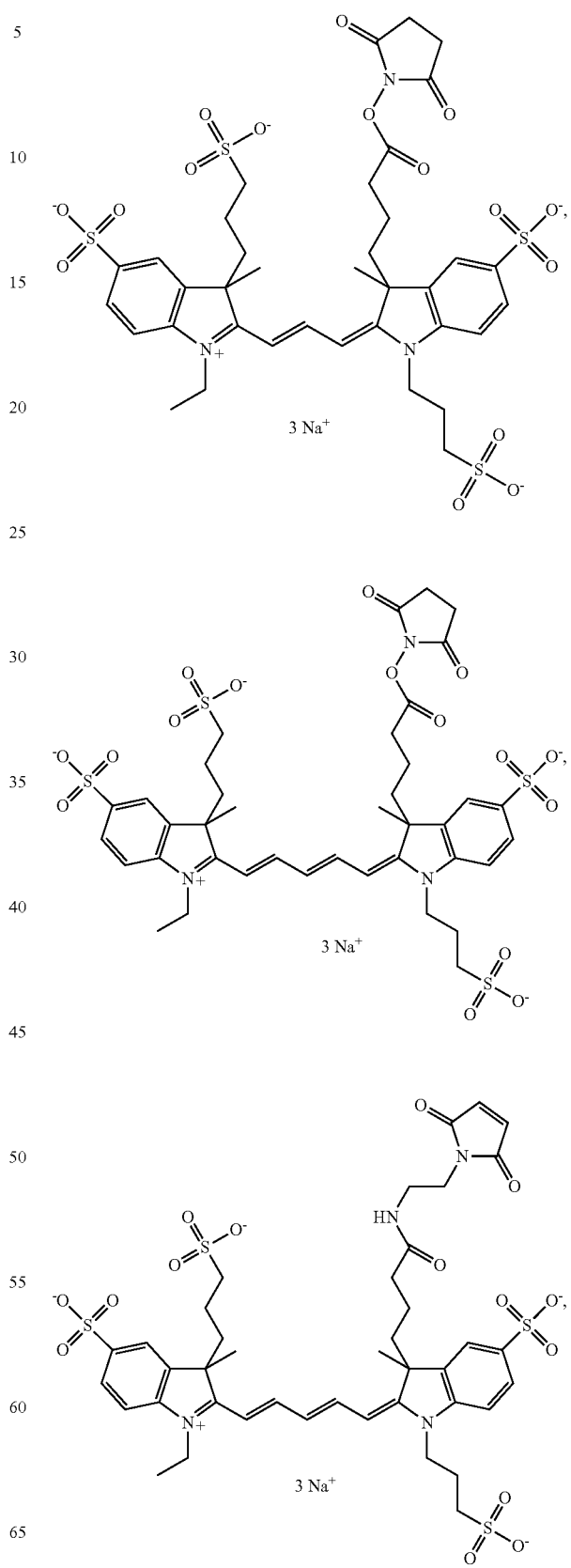

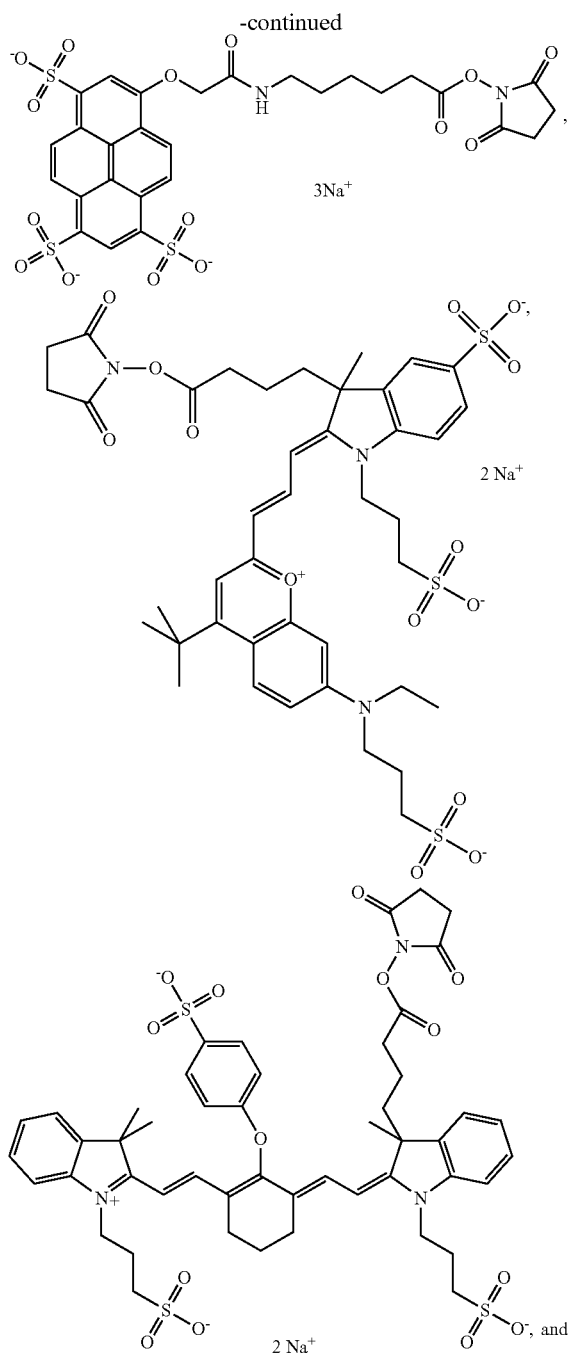

fluorescent derivatives thereof.

21. A method for selecting a detector for use in flow cytometry comprising:
  (a) obtaining a spectrum of at least one dye in a form capable of being operated on by a dieital computing device,
  (b) obtaining a laser and optical filter configuration for each of a plurality of detectors in a form capable of being operated on by a digital computing device,
  (c) obtainin, via a digital computing device, for each of a plurality of combinations of the at least one dye and a detector configuration, a spectrum yield value,
  (d) ranking the spectrum yield values,
  (e) selecting a detector based upon ranking of the spectrum yield values in step (d) wherein the detector produces a maximum spectrum yield value in relation to the bandwidth of the optical filter.

22. The method according to claim 21, wherein the spectrum is an excitation spectrum.

23. The method according to claim 21, wherein the spectrum is an emission spectrum.

24. The method according to claim 21, wherein the detector of step (b) is a component of a flow cytometer.

25. The method according to claim 21, wherein the spectrum yield value in step (c) is obtained for a plurality of dyes.

26. The method according to claim 21, wherein the dye in step (a) wherein the dye in step (a) is selected from the group consisting of fluorescein isothiocyanate, R-phycoerythrin, a tandem conjugate of sulforhodamine 101 acid chloride with R-phycoerythrin, a tandem conjugate of 1-($\epsilon$-carboxypentyl)-1'-ethyl-3,3,3',3'-tetramethylindodicarbocyanine-5,5'-disulfonate potassium salt N-hydroxysuccinimide ester with R-phycoerythrin, enhanced green fluorescent protein, enhanced yellow fluorescent protein, DsRed, allophycocyanin, peridinin chlorophyll protein coumarin 3-($\epsilon$-carboxypentyl)-3'-ethyl -oxacarbocyanine-6,6'-disulfonate potassium salt N-hydroxysuccinimide ester, 1-($\epsilon$-carboxypentyl) -1'-ethyl-3,3,3',3'-tetramethylindocarbocyanine-5,5'-disulfonate potassium salt N-hydroxysuccinimide ester, 1-($\epsilon$-carboxypentyl)-1'-ethyl-3,3,3',3'-tetramethyl-3H-benz (e)indocarbocyanine-5,5',7,7'-tetrasulfonate tripotassium salt N-hydroxysuccinimide ester, 1-($\epsilon$-carboxypentyl)-1'-ethyl-3,3,3',3'-tetramethylindodicarbocyanine-5,5'-disulfonate potassium salt N-hydroxysuccinimide ester, 1-($\epsilon$-carboxypentyl)-1'-ethyl-3,3,3',3'-tetramethyl -3H-benz(e)indodicarbocyanine-5,5',7,7'-tetrasulfonate tripotassium salt N-hydroxysuccinimide ester, 1-($\epsilon$-carboxypentyl)-1'-ethyl-3,3,3', 3'-tetramethylindotricarbocyanine -5,5'-disulfonate potassium salt N-hydroxysuccinimide ester, 2'-(4-ethoxyphenyl)-5-(4-methyl-1-piperazinyl)-5'-bi-1H-benzimidazole, 2-[4-(aminoiminomethyl) phenyl]-1H-indole-6-carboximidamide, Phenol, 4-[5-(4-methyl-1-piperazinyl) [2,5'-bi-1H-benzimidazo]-2'-yl]-, trihydrochloride chromomycin A3, mithramycin, Quinolinium, 1,1-[1,3- propanediylbis [(dimethyliminio)-3,1-propanediyl]]bis[4-[(3-methyl-2 (3H)- benzoxazolylidene)methyl]]-, tetraiodide, ethidium bromide, 7-aminoactinomycin D, acridine orange, Quinolinium, 1-1-[1,3-propanediylbis[(dimethyliminio)-3,1-propanediyl]]bis[4-[(3-methyl-2(3H) -benzothiazolylidene)methyl]]-, tetraiodide, Quinolinium, 4-[(3-methyl-2(3H)-benzothiazolylidene) methyl]-1-[3-(trimethylammonio) propyl]-, diiodide, quinolinium, 1-methyl-4-((3-methyl-2 (3H)-benzothiazolylidene)methyl), salt with 4-methylbenzenesulfonic acid (1:1), Quinolinium, 1,1'-[1,3-propanediylbis [(dimethylminio)-3,1-propanediyl]]bis[4-[3-(3-methyl-2(3H)-benzothiazolylidene)-1-propenyl]-, tetraiodide, Quinolinium, 4-[3-(3-methyl-2(3H)-benzothiazolylidene)-1-propenyl]-1-[3-(trimethylammonio) propyl]-, diiodide, propidium iodide, LDS 751, 2-[4-[bis(carboxymethyl)amino]-3-[2-[2-[bis(carboxymethyl)amino]-5-methylphenoxy]ethoxyl]phenyl]-1H-indole-6-carboxylic acid, N-[2-[2-[2-[bis(carboxymethyl)amino]-5-(2,7-dichloro-6-hdroxy-3-oxo-3H-xanthen-9-yl) phenoxyl] ethoxy]-4-methylphenyl]-N-(carboxymethyl)-glycine, dichlorodihydrofluorescein diacetate, dihydrorhodamine, SNARF, Y66F , Y66H, enhanced blue fluorescent protein, green fluorescent protein uv, enhanced cyan fluorescent protein, green fluorescent protein, AmCyan1, Y77W, S65A, S65C, S65L, S65T, ZsGreen1, ZsYellow1, DsRed2, DsRed monomer, AsRed2, mRFP1, HcRed1, monochlorobimane, calcein, cyanine, hydroxycoumarin, aminocoumarin, methoxycoumarin, acetic acid, [(3,6,8-trisulfo-1-pyrenyl)oxy]-, 1-hydrazide, trisodium salt, 1H-Benz[de]lisoquinoline-5,8-disulfonic acid, 6-amino-2-[(hydrazinocarbonyl)aminol]-2,3-dihydro-1,3-dioxo-, dilithium salt, 6-[(7-nitro-2, 1,3-benzoxadiazol-4-yl)aminol-hexanoic acid, conjugates of 1-(ε-carboxypentyl) -1'-ethyl-3,3,3',3'-tetramethylindotricarbocyanine-5,5'-disulfonate potassium salt N-hydroxysuccinimide ester with R-phycoerythrin, conjugates of allophycocyanin with 1-(ε-carboxypentyl)-1'-ethyl-3,3,3',3'-tetramethylindotricarbocyanine-5, 5'-disulfonate potassium salt N-hydroxysuccinimide ester, Red 613, fluorescein, 6-(5-and 6-fluoresceinyl-carboxamido)-hexanoic acid N-hydroxysuccinimide ester, 4,4-difluoro-5,7-dimethyl-4-bora-3a,4a-diaza-s-indacene-3-propionic acid tetramethylrhodamine-6-isothiocyanate, X-rhodamine, lissamine rhodamine B, sulforhodamine 101 acid chloride, conjugate of peridinin chlorophyll protein with 1-(ε-carboxypentyl) -1'-ethyl-3,3,3',3'-tetramethyl-3H-benz(e)indodicarbocyanine-5,5',7,7'tetrasulfonate tripotassium salt N-hydroxysuccinimide ester, and fluorescent derivatives thereof.

27. The method according to claim 21, further comprising performing the ranking step on the digital computing device programmed with software to perform the ranking step.

28. The method according to claim 21, wherein the dye in step (a) comprises a compound selected from the group consisting of

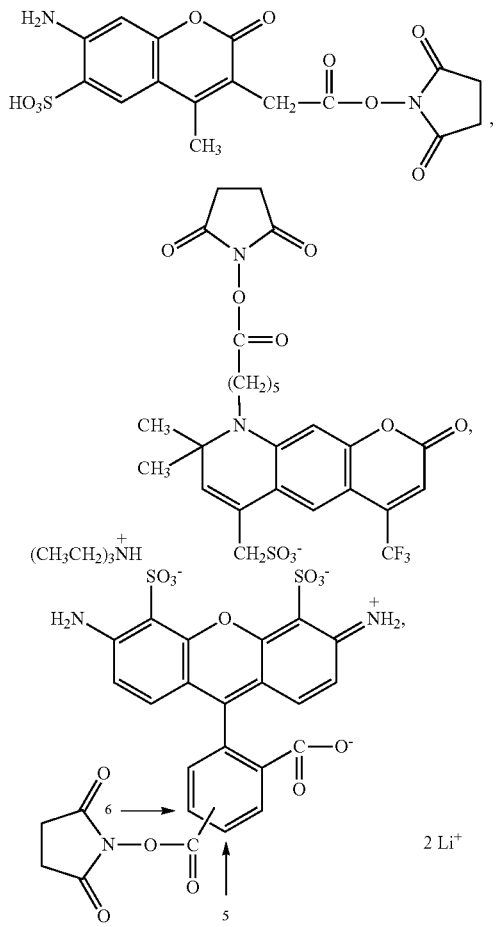

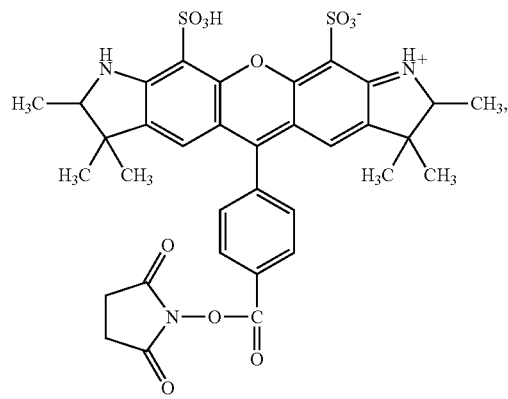

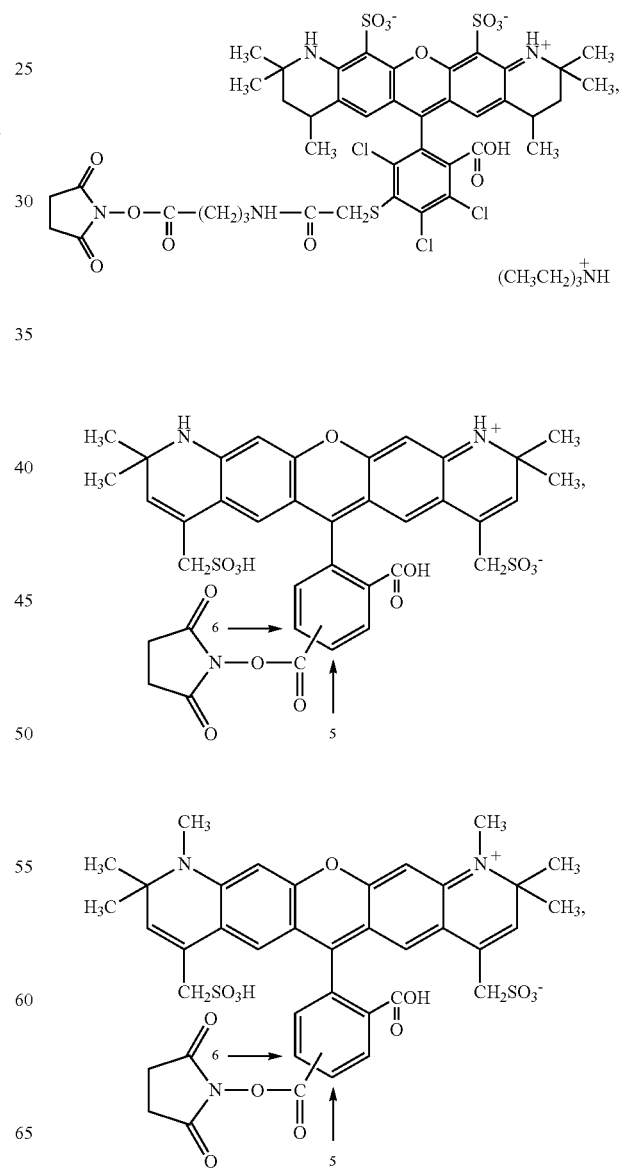

33
-continued

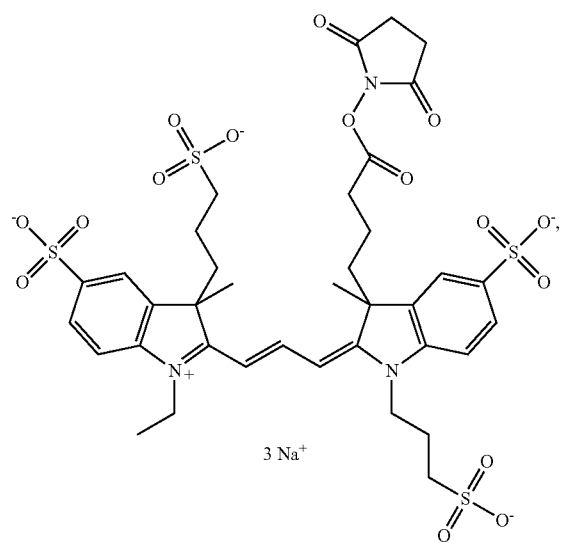

3 Na⁺

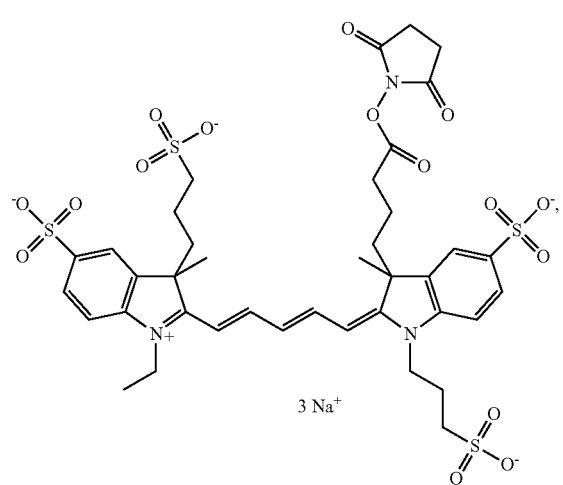

3 Na⁺

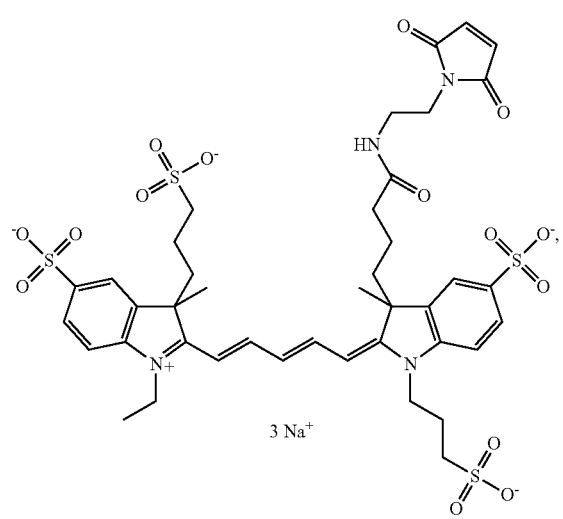

3 Na⁺

34
-continued

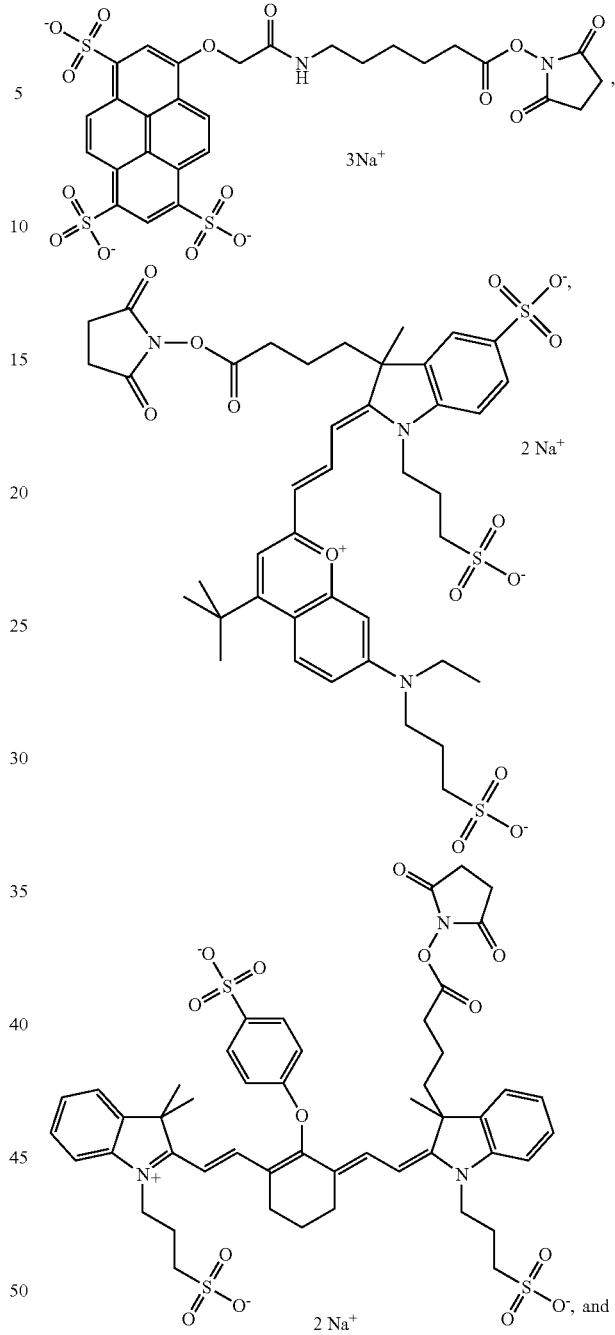

fluorescent derivatives thereof.

29. A particle analysis mechanism, comprising:
a stimulation emission mechanism, emitting a stimulation emission having a spectrum;
a particle marked with a material responsive to the stimulation emission;
a particle response detector, having a configuration, detecting a response coming from the material;
the stimulation emission mechanism and the response detector having been selected based criteria determined according to the following:
obtaining the spectrum of the stimulation emission;
obtaining a spectrum yield based upon the stimulation emission spectrum and the configuration;

repeating the obtaining the spectrum and the obtaining the spectrum yield for a plurality of combinations of the emission spectrum and the configuration;

ranking the spectrum yields for the plurality of combinations; and, selecting the stimulation emission mechanism and the response detector based upon the ranking of the spectrum yields for the different combinations.

30. The particle analysis mechanism of claim 29 further comprising:

the response detector configuration comprising a light source configuration and a filter configuration.

31. The particle analysis mechanism of claim 29 further comprising:

the response detector configuration comprising a light detector detecting light within a detection spectrum and a filter selected based upon the response detector detection spectrum.

32. The particle analysis mechanism of claim 29 comprising:

a flow cytometry particle analyzer.

33. The particle analysis mechanism of claim 29 further comprising:

the stimulation emission mechanism comprising a light source.

34. The particle analysis mechanism of claim 29 further comprising:

the material comprising a dye.

35. A particle analysis mechanism, comprising:

a stimulation emission mechanism, emitting a stimulation emission having a spectrum;

a particle marked with a material responsive to the stimulation emission;

a particle response detector, having a configuration, detecting a response coming from the material;

the material having been selected based on criteria determined according to the following:

obtaining the spectrum of the stimulation emission;

obtaining a spectrum yield based upon the stimulation emission spectrum and the material and the configuration;

repeating the obtaining the spectrum and the obtaining the spectrum yield for a plurality of combinations of the emission spectrum, the material and the configuration;

ranking the spectrum yields for the plurality of combinations; and, selecting the material based upon the ranking of the spectrum yields for the different combinations.

36. A particle analysis mechanism, comprising:

a stimulation emission mechanism, emitting a stimulation emission having a spectrum;

a particle marked with a material responsive to the stimulation emission;

a particle response detector, having a configuration, detecting a response coming from the material;

the response detector having been selected based criteria determined according to the following:

obtaining the spectrum of the stimulation emission;

obtaining a spectrum yield based upon the stimulation emission spectrum and the material and the configuration;

repeating the obtaining the spectrum and the obtaining the spectrum yield for a plurality of combinations of the emission spectrum, the material and the configuration;

ranking the spectrum yields for the plurality of combinations; and, selecting the response detector based upon the ranking of the spectrum yields for the different combinations.

37. The particle analysis mechanism of claim 36 further comprising:

the response detector comprising a light detector detecting light within a detection spectrum and a filter selected based upon the response detector detection spectrum.

38. The particle analysis mechanism of claim 36 further comprising:

the response detector comprising a plurality of response detectors.

* * * * *